United States Patent [19]

Osborn, III et al.

[11] Patent Number: 5,674,212
[45] Date of Patent: Oct. 7, 1997

[54] EXTENSIBLE ABSORBENT ARTICLES

[75] Inventors: Thomas W. Osborn, III, Cincinnati, Ohio; Kazuko Sugahara, Osaka, Japan; Letha M. Hines, Cincinnati, Ohio

[73] Assignee: The Procter & Gamble Company, Cincinnati, Ohio

[21] Appl. No.: 503,895

[22] Filed: Jul. 18, 1995

Related U.S. Application Data

[63] Continuation of Ser. No. 915,284, Jul. 23, 1992, abandoned, which is a continuation of Ser. No. 315,315, Sep. 29, 1994, which is a continuation-in-part of Ser. No. 539,779, Oct. 12, 1990, abandoned, Ser. No. 605,583, Oct. 29, 1990, abandoned, Ser. No. 630,451, Dec. 19, 1990, abandoned, Ser. No. 637,090, Jan. 3, 1991, abandoned, Ser. No. 637,571, Jan. 3, 1991, abandoned, Ser. No. 769,891, Oct. 1, 1991, abandoned, Ser. No. 769,607, Oct. 1, 1991, abandoned, Ser. No. 734,392, Jul. 23, 1991, abandoned, Ser. No. 734,404, Jul. 23, 1991, abandoned, Ser. No. 734,405, Jul. 23, 1991, Pat. No. 5,334,176, Ser. No. 794,745, Nov. 19, 1991, abandoned, Ser. No. 810,774, Dec. 17, 1991, abandoned, Ser. No. 823,797, Jan. 22, 1992, abandoned, Ser. No. 827,555, Jan. 28, 1992, abandoned, Ser. No. 832,246, Feb. 7, 1992, Ser. No. 874, 872, Apr. 28, 1992, abandoned, Ser. No. 882,738, May 14, 1992, abandoned, and Ser. No. 892,398, May 28, 1992, abandoned.

[51] Int. Cl.⁶ ........................................................ A61F 13/15
[52] U.S. Cl. ........................ 604/385.1; 604/387; 604/373
[58] Field of Search ........................................ 604/358, 373, 604/383, 384, 385.1, 385.3, 387

[56] References Cited

U.S. PATENT DOCUMENTS

| | | |
|---|---|---|
| Re. 30,057 | 7/1979 | Schaar . |
| 810,119 | 1/1906 | Green . |
| 2,701,567 | 2/1955 | Smith . |
| 2,705,497 | 4/1955 | Johnson et al. . |
| 3,214,323 | 10/1965 | Russell et al. ............... 604/373 |
| 3,339,548 | 9/1967 | Seltzer . |
| 3,371,668 | 3/1968 | Johnson ....................... 604/373 |
| 3,427,670 | 2/1969 | Nimoy ......................... 604/373 |
| 3,561,446 | 2/1971 | Jones, Sr. . |
| 3,570,493 | 3/1971 | Olsson . |
| 3,653,382 | 4/1972 | Easley et al. . |

(List continued on next page.)

FOREIGN PATENT DOCUMENTS

| | | |
|---|---|---|
| 0 234 194 | 9/1987 | European Pat. Off. . |
| 0 321 985 A2 | 6/1989 | European Pat. Off. . |
| 0 359 502 A2 | 3/1990 | European Pat. Off. . |
| 0 426 235 A2 | 5/1991 | European Pat. Off. . |
| 0 432 755 A1 | 6/1991 | European Pat. Off. . |
| 0 432 763 A1 | 6/1991 | European Pat. Off. . |
| 0 433 951 A2 | 6/1991 | European Pat. Off. . |
| 0 293 208 A1 | 7/1991 | European Pat. Off. . |
| 0 450 541 A2 | 10/1991 | European Pat. Off. . |
| 0 467 409 A1 | 1/1992 | European Pat. Off. . |
| 0 472 942 A1 | 3/1992 | European Pat. Off. . |
| 0 506 336 A1 | 9/1992 | European Pat. Off. . |
| 0 506 957 A1 | 10/1992 | European Pat. Off. . |
| 0 511 905 A1 | 11/1992 | European Pat. Off. . |
| 513 876 | 8/1929 | Germany . |
| 40-36391 | 12/1965 | Japan . |
| 2 168 253 | 6/1986 | United Kingdom . |
| WO 91/00720 | 1/1991 | WIPO . |
| WO 91/09581 | 7/1991 | WIPO . |
| WO 92/04183 | 3/1992 | WIPO . |
| WO 92/07535 | 5/1992 | WIPO . |
| WO 92/14429 | 9/1992 | WIPO . |
| WO 92/15444 | 9/1992 | WIPO . |
| WO 92/15445 | 9/1992 | WIPO . |
| WO 92/15446 | 9/1992 | WIPO . |
| WO 93/06805 | 4/1993 | WIPO . |
| WO 93/12747 | 7/1993 | WIPO . |
| WO 93/15248 | 8/1993 | WIPO . |
| WO 93/15249 | 8/1993 | WIPO . |
| WO 93/15251 | 8/1993 | WIPO . |
| WO 93/18729 | 9/1993 | WIPO . |

*Primary Examiner*—Robert A. H. Clarke
*Attorney, Agent, or Firm*—Jeffrey V. Bamber; Steven W. Miller; E. Kelly Linman

[57] ABSTRACT

The present invention relates to absorbent articles such as sanitary napkins worn by women. More particularly, the present invention relates to absorbent articles, such as thin sanitary napkins, that are extensible, especially in the longitudinal direction.

27 Claims, 15 Drawing Sheets

U.S. PATENT DOCUMENTS

| | | |
|---|---|---|
| 3,672,371 | 6/1972 | Roeder . |
| 3,717,150 | 2/1973 | Schwartz . |
| 3,727,615 | 4/1973 | Duchane . |
| 3,776,233 | 12/1973 | Schaar . |
| 3,848,599 | 11/1974 | Schaar . |
| 3,885,568 | 5/1975 | Schaar . |
| 3,888,255 | 6/1975 | Shah et al. ............................ 604/323 |
| 3,981,306 | 9/1976 | Krusko . |
| 3,995,640 | 12/1976 | Schaar . |
| 4,013,816 | 3/1977 | Sabee et al. . |
| 4,023,571 | 5/1977 | Comerford et al. . |
| 4,036,233 | 7/1977 | Kozak . |
| 4,041,949 | 8/1977 | Kozak . |
| 4,050,462 | 9/1977 | Woon et al. . |
| 4,062,995 | 12/1977 | Korpman . |
| 4,166,464 | 9/1979 | Korpman . |
| 4,176,667 | 12/1979 | Herring . |
| 4,226,238 | 10/1980 | Bianco . |
| 4,232,674 | 11/1980 | Melican . |
| 4,235,237 | 11/1980 | Mesek et al. . |
| 4,269,188 | 5/1981 | Nishizawa et al. . |
| 4,318,408 | 3/1982 | Korpman ............................. 604/373 |
| 4,425,130 | 1/1984 | DesMarais . |
| 4,450,026 | 5/1984 | Rieniaki et al. . |
| 4,505,707 | 3/1985 | Feeney . |
| 4,545,372 | 10/1985 | Lauritzen . |
| 4,573,991 | 3/1986 | Pieniak et al. . |
| 4,578,070 | 3/1986 | Holtman . |
| 4,596,570 | 6/1986 | Jackson et al. . |
| 4,597,759 | 7/1986 | Johnson . |
| 4,655,760 | 4/1987 | Morman et al. . |
| 4,657,802 | 4/1987 | Morman . |
| 4,662,874 | 5/1987 | Korpman . |
| 4,681,580 | 7/1987 | Reising et al. . |
| 4,690,680 | 9/1987 | Higgins . |
| 4,692,163 | 9/1987 | Widlund et al. . |
| 4,699,620 | 10/1987 | Bernardin . |
| 4,710,187 | 12/1987 | Boland et al. . |
| 4,731,066 | 3/1988 | Korpman . |
| 4,747,846 | 5/1988 | Boland et al. . |
| 4,750,482 | 6/1988 | Sieverding . |
| 4,753,648 | 6/1988 | Jackson . |
| 4,758,241 | 7/1988 | Papajohn . |
| 4,798,604 | 1/1989 | Carter . |
| 4,834,736 | 5/1989 | Boland et al. . |
| 4,834,738 | 5/1989 | Kielpikowski et al. . |
| 4,847,134 | 7/1989 | Fahrenkrug et al. . |
| 4,857,067 | 8/1989 | Wood et al. . |
| 4,886,512 | 12/1989 | Damico et al. . |
| 4,891,258 | 1/1990 | Fahrenkrug . |
| 4,900,320 | 2/1990 | McCoy . |
| 4,911,701 | 3/1990 | Mavinkurve . |
| 4,917,697 | 4/1990 | Osborn, III et al. . |
| 4,940,462 | 7/1990 | Salerno . |
| 4,941,933 | 7/1990 | Korpman . |
| 4,950,262 | 8/1990 | Takagi . |
| 4,950,264 | 8/1990 | Osborn, III . |
| 4,957,795 | 9/1990 | Riedel ...................................... 604/373 |
| 4,965,122 | 10/1990 | Morman . |
| 4,992,324 | 2/1991 | Dube . |
| 5,007,906 | 4/1991 | Osborn, III et al. . |
| 5,009,653 | 4/1991 | Osborn, III . |
| 5,011,480 | 4/1991 | Gossens et al. . |
| 5,013,382 | 5/1991 | Nalewaniec et al. . |
| 5,026,458 | 6/1991 | Beuther . |
| 5,032,120 | 7/1991 | Freeland et al. . |
| 5,037,415 | 8/1991 | Leroy et al. . |
| 5,037,416 | 8/1991 | Allen et al. . |
| 5,037,417 | 8/1991 | Terhstrom . |
| 5,114,781 | 5/1992 | Morman . |
| 5,116,662 | 5/1992 | Morman . |
| 5,129,893 | 7/1992 | Thoren . |
| 5,139,841 | 8/1992 | Makoui et al. . |
| 5,143,679 | 9/1992 | Weber et al. . |
| 5,151,320 | 9/1992 | Homonoff et al. . |
| 5,156,793 | 10/1992 | Buell et al. . |
| 5,169,706 | 12/1992 | Collier, IV et al. . |
| 5,171,239 | 12/1992 | Igaue et al. . |
| 5,171,302 | 12/1992 | Buell . |
| 5,197,959 | 3/1993 | Buell . |
| 5,234,422 | 8/1993 | Sneller et al. . |
| 5,234,442 | 8/1993 | Sneller et al. . |
| 5,260,126 | 11/1993 | Collier . |
| 5,267,992 | 12/1993 | Van Tilburg . |
| 5,269,775 | 12/1993 | Freeland et al. . |
| 5,281,208 | 1/1994 | Thompson et al. . |
| 5,308,346 | 5/1994 | Sneller et al. . |
| 5,334,176 | 8/1994 | Buenger et al. . |
| 5,342,341 | 8/1994 | Igaue et al. . |
| 5,344,691 | 9/1994 | Manschen et al. . |
| 5,346,486 | 9/1994 | Osborn et al. . |
| 5,356,405 | 10/1994 | Thompson et al. . |
| 5,376,198 | 12/1994 | Fahrenkrug et al. . |
| 5,382,245 | 1/1995 | Thompson et al. . |
| 5,382,467 | 1/1995 | Widlund et al. . |
| 5,411,498 | 5/1995 | Fahrenkrug et al. . |
| 5,431,991 | 7/1995 | Quantrille et al. . |

| | LONGITUDINAL | | | WIDTH | | | ELASTIC WALL | |
|---|---|---|---|---|---|---|---|---|
| | % LONGITUDINAL STRETCH | g. OF FORCE TO EXTEND PAD | % PAD SET | % WIDTH STRETCH | g. OF FORCE TO EXTEND 1.0" STRIP | % PAD SET | % STRETCH | g. FORCE |
| CONDITIONS FOR STRETCH | 40% | ≤1000 g. ≤800 g. | ≤10 ≤10 ≤25 | 40% | ≤500 g. ≤400 g. | ≤10 ≤25 | 50% | 1500 g. 2000 g. |
| | 25% | ≤800 g. ≤400 g. ≤300 g. | ≤10 ≤25 | 25% | ≤500 g. ≤400 g. | ≤10 ≤25 | 40% | 1500 g. 2000 g. |
| | | | | | | | 25% | 1500 g. 2000 g. |
| MINIMUM FORCE TO STRETCH | 25% | ≥50 g. | | | | | | |

Table 1...Typical Values for Stretch Parameters

Fig. 8

EXTENSIBLE ABSORBENT ARTICLES

CROSS-REFERENCE TO RELATED APPLICATIONS

This is a continuation of application Ser. No 07/915,284, filed on Jul. 23, 1992 now abandon which is a continuation of application Ser. No. 08/315,315, filed on Sep. 29, 1994, which a continuation-in-part of the following U.S. patent applications: Ser. No. 07/539,779 abandoned filed Sep. 12, 1990; Ser. No. 07/605,583 abandoned filed Oct. 29, 1990; Ser. No. 07/630,451 abandoned filed Dec. 19, 1990; Ser. Nos. 07/637,090 abandoned and 07/637,571 abandoned filed Jan. 3, 1991; Ser. Nos. 07/769,891 abandoned and 07/769,607 abandoned filed Oct. 1, 1991; Ser. Nos. 07/734,392, abandoned 07/734,404 abandoned, and 07/734,405 now U.S. Pat. No. 5,334,176 filed Jul. 23, 1991; Ser. No. 07/794,745 filed Nov. 19, 1991 now abandoned; Ser. No. 07/810,774 filed Dec. 17, 1991; abandoned Ser. No. 07/823,797 filed Jan. 22, 1992 now abandoned; Ser. No. 07/827,555 filed Jan. 28, 1992 ; now abandoned Ser. No. 07/832,246 filed Feb. 7, 1992; Ser. No. 07/874,872 filed Apr. 28, 1992 now abandoned ; Ser. No. 07/882,738 filed May 14,1992 now abandoned ; and, Ser. No. 07/892,398 filed May 28, 1992 abandoned.

FIELD OF THE INVENTION

The present invention relates to absorbent articles such as sanitary napkins, panty liners, and incontinent pads. More particularly, the present invention relates to sanitary napkins that are extensible or, more preferably stretchable, especially in the longitudinal direction.

BACKGROUND OF THE INVENTION

Absorbent articles such as sanitary napkins, pantiliners, and incontinent pads are designed to absorb and retain liquid and other discharges from the human body and to prevent body and clothing soiling. Sanitary napkins are a type of absorbent article worn by women that is normally positioned between the wearer's legs, adjacent to the perineal area of the body.

Typically, most of the disposable absorbent articles of the types mentioned above are made of materials that will not stretch. That is, the materials (and the article itself) will not stretch under the forces that the absorbent article is normally subjected to when worn.

The inability of the absorbent articles to stretch causes such articles to have a number of serious drawbacks. One of the most serious is that they are not as comfortable for the wearer as they could be. The wearer should ideally be able to notice a difference between an absorbent article that stretches to conform to the wearer's body and with the wearer's movements and an absorbent article that fails to stretch. Conventional sanitary napkins will also fail to move with the wearer's undergarments, causing the sanitary napkins to shift. Providing the sanitary napkin with stretch properties will permit the napkin to better conform to the wearer's undergarment and stay in place. Several patent publications disclose absorbent articles having various components that are capable of stretching. Such efforts are described in U.S. Pat. No. 2,701,567 issued to Smith, U.S. Pat. No. 3,570,493 issued to Olsson, U.S. Pat. No. 3,653,382 issued to Easley, et al., U.S. Pat. No. 3,717,150, issued to Schwartz, U.S. Pat. No. 4,013,816 issued to Sabee, et al., U.S. Pat. No. 4,041,949 issued to Kozak, U.S. Pat. No. 4,166,464 issued to Korpman, U.S. Pat. No. 4,533,357 issued to Hall, U.S. Pat. No. 4,573,991 issued to Pieniak, et al., U.S. Pat. No. 4,578,070 issued to Holtman, U.S. Pat. No. 4,596,570 issued to Jackson, et al., U.S. Pat. No. 4,655,760 issued to Morman, et al. U.S. Pat. No. 4,731,066 issued to Korpman, U.S. Pat. No. 4,847,134 issued to Fahrenkrug, et al., U.S. Pat. No. 4,891,258 issued to Fahrenkrug, et al., U.S. Pat. No. 4,965,122 issued to Morman, U.S. Pat. No. 4,992,324 issued to Dube, U.S. Pat. No. 5,011,480 issued to Gossens, et al., and European Patent Application 0 450 541 A2 published in the name of Morris, et al.

The publications listed above may disclose providing absorbent articles with one or more stretchable components. The present invention, however, is directed to absorbent articles, such as sanitary napkins, that in a number of embodiments are comprised entirely of components capable of stretching to accommodate the movements of the wearer and the wearer's undergarments. The present application also is directed to a vast number of embodiments for utilizing stretch properties to improve the fit of the absorbent article.

It is an object of this invention to provide an absorbent article, particularly a relatively thin absorbent article, such as a sanitary napkin, that is capable of extending, or more preferably, stretching.

It is a particular object of this invention to provide such an absorbent article that is capable of extending (and preferably stretching) in the longitudinal direction when the article is worn for improved comfort and fit.

These and other objects of the present invention will be more readily apparent when considered in reference to the following description and when taken in conjunction with the accompanying drawings.

SUMMARY OF THE INVENTION

The present invention provides an absorbent article, such as a sanitary napkin. The sanitary napkin of the present invention is capable of extending.

The sanitary napkin, however, may be extensible in length (i.e., in the longitudinal direction) and/or width (i.e., in the transverse direction), and/or in other directions. The sanitary napkin is preferably also elastically extensible.

The sanitary napkin of the present invention, in one embodiment comprises an extensible liquid pervious topsheet, an extensible liquid impervious backsheet, and an extensible absorbent core. The absorbent core is positioned between the topsheet and the backsheet. The topsheet and backsheet are joined together around the periphery of the sanitary napkin. The sanitary napkin also comprises a fastener for attaching the sanitary napkin to the crotch region of the wearer's panties. The fastener is capable of permitting at least portions of the sanitary napkin to extend in the longitudinal direction.

A number of different types of structures suitable for the above components of the sanitary napkin are disclosed. A number of alternative embodiments for the overall structure of the sanitary napkin are also disclosed.

In several alternative embodiments, the sanitary napkin is comprised of some extensible components and some inextensible components. For instance, the sanitary napkin may have an extensible topsheet and backsheet and an inextensible absorbent core that is slung between the extensible topsheet and backsheet. In a variation of such an embodiment, the sanitary napkin may have an inextensible topsheet as well.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings (which are not necessarily to scale), in which like designations are used to designate substantially identical elements, and in which:

FIG. 8 is a table which shows the preferred relationship between the magnitude of stretching forces applied to the sanitary napkin and the amount the sanitary napkin stretches in response to such forces.

DETAILED DESCRIPTION OF THE INVENTION

1. Overall Characteristics of the Absorbent Article

The overall characteristics of the absorbent article of the present invention will be discussed first.

Figure 1:
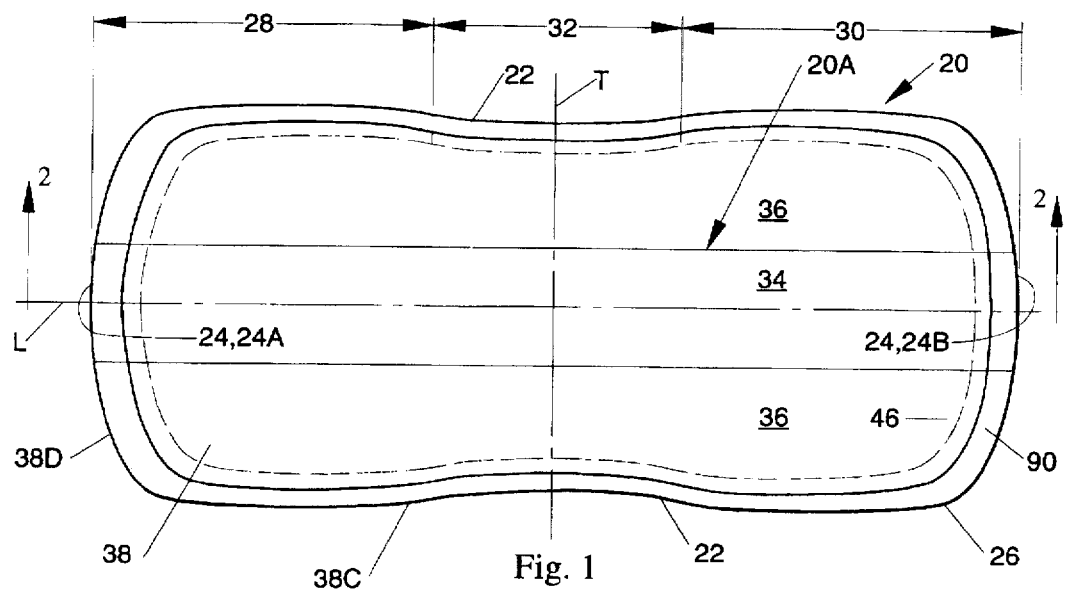
FIG. 1 is a top plan view of a stretchable sanitary napkin according to the present invention in unstretched condition.
Figure 2:
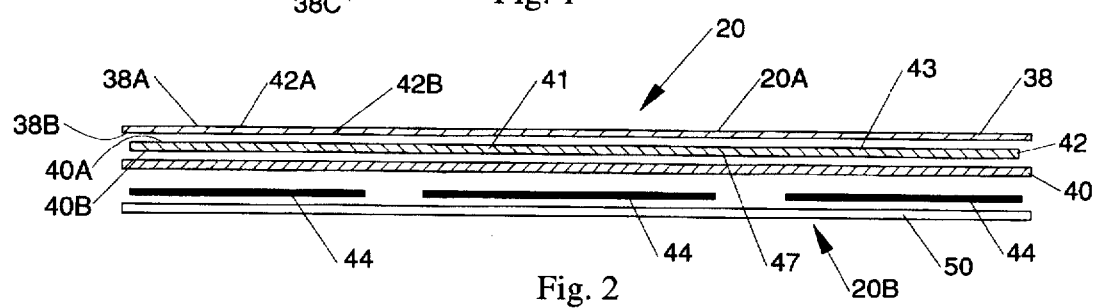
FIG. 2 is a schematic sectional view taken along line 2—2 of the sanitary napkin shown in FIG. 1 in a disassembled condition.
Figure 3:
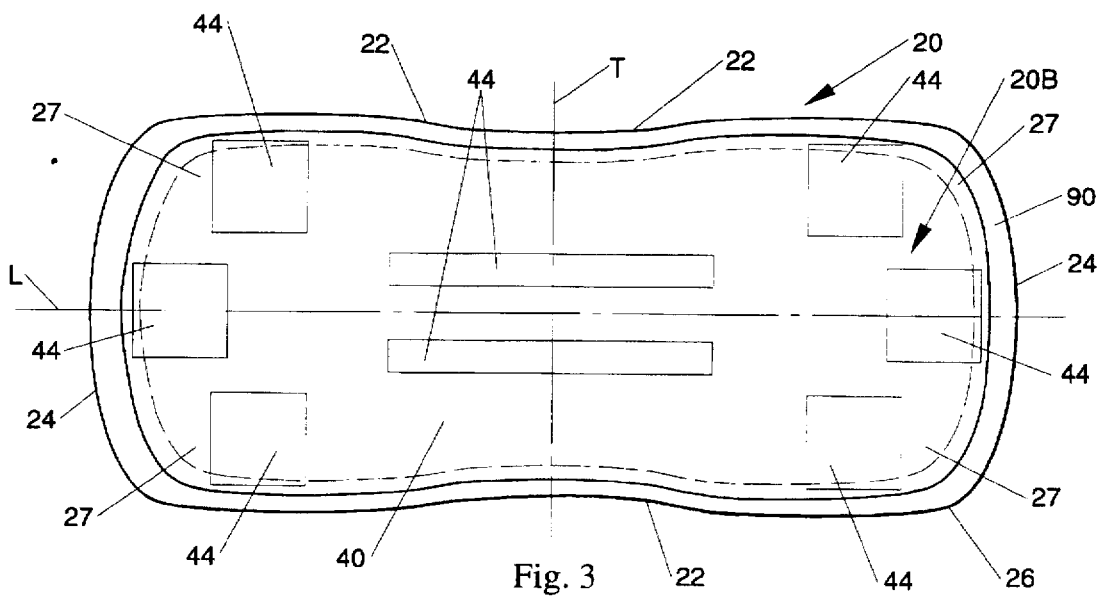
FIG. 3 is a bottom plan view of the sanitary napkin shown in FIG. 1 without the optional adhesive cover strip.

FIGS. 1–3 show a preferred embodiment of a disposable absorbent article of the present invention. The present invention relates to absorbent articles, such as sanitary napkins. More particularly, the present invention relates to thin sanitary napkins that are stretchable, especially in the longitudinal direction.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (and other articles worn in the crotch region of a garment).

The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the sanitary napkin 20 also has two spaced apart longitudinal edges 22 and two spaced apart transverse or end edges (or "ends") 24, which together form the periphery 26 of the sanitary napkin 20. When the sanitary napkin 20 is worn, one of the end edges 24 will be oriented toward the front of the wearer, and one of the end edges 24 will be oriented toward the rear of the wearer. The end edge 24 oriented toward the front of the wearer is designated 24A, and the end edge oriented toward the rear of the wearer is designated 24B.

The sanitary napkin has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the sanitary napkin. A detailed description of the central region 32 and the two end regions 28 and 30 is contained in U.S. Pat. No. 4,690,680 issued to Higgins on Sep. 1, 1987.

The sanitary napkin also has a longitudinally-oriented (or longitudinal central region 34 disposed along the length of at least a portion of the longitudinal centerline L, and longitudinal side regions 36 laterally outboard of the longitudinal central region 34.

The sanitary napkin 20 can be of any thickness, including relatively thick, relatively thin, or even very thin. The embodiment of the sanitary napkin 20 shown in FIGS. 1–3 of the drawings is intended to be an example of a relatively thin sanitary napkin, preferably an "ultra-thin" sanitary napkin. It should be understood, however, when viewing these figures the number of layers of material shown cause the sanitary napkin 20 to appear much thicker than it actually is. An "ultra-thin" sanitary napkin 20 preferably has a caliper of less than about 3 millimeters. The thin sanitary napkin 20 shown should also be preferably relatively flexible, so that it is comfortable for the wearer.

FIG. 2 shows the individual components of the sanitary napkin. The sanitary napkin 20 of the present invention generally comprises at least four primary components. These include a liquid pervious topsheet 38, a liquid impervious backsheet (or "barrier means") 40, an absorbent core 42, and a fastener 44 for attaching the sanitary napkin to the wearer's panties. The absorbent core 42 is positioned between the topsheet 38 and the backsheet 40.

The sanitary napkin 20 of the present invention can also be provided with any optional additional components. The optional components may include, but are not limited to one or more wicking layers 46 (such as the aquisition layer or the "secondary topsheet" shown in FIG. 6), an optional interliner 48 (FIG. 51), side flaps 52 (FIG. 5), and a removable cover strip or release liner 50 (FIG. 2). The wicking layer 46 may be positioned between the topsheet 38 and the absorbent core 42. As shown in FIG. 51 the optional interliner 48 is positioned between the absorbent core 42 and the backsheet 40. The side flaps or "wings" 52 are folded around the crotch portion of the wearer's panties. (The wearer's panties or undergarments are designated U in the drawings.) The removable release liner 50 covers the fasteners 44 when they comprise adhesives. This keeps the adhesives from sticking to surfaces other than the crotch portion of the undergarment prior to use of the sanitary napkin 20.

Figure 4:
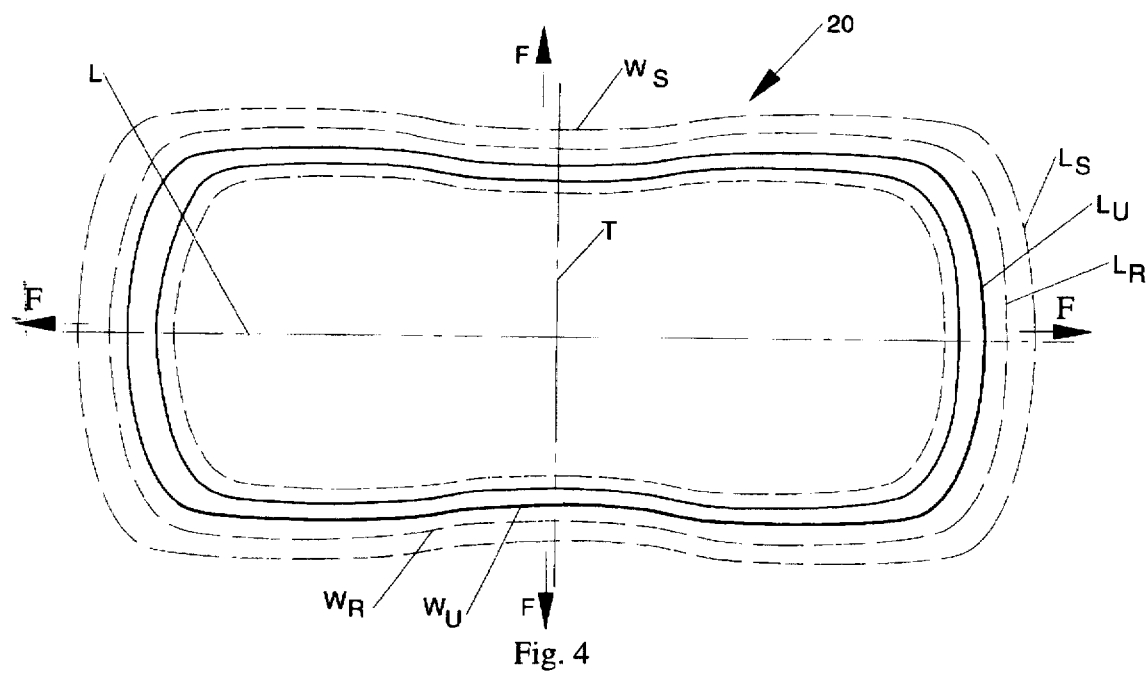
FIG. 4 is a top plan view taken which shows the sanitary napkin in FIG. 1 after stretching.

The extensibility of the sanitary napkin 20 is shown in FIG. 4. The term "extensible", as used herein refers to articles that can increase in at least one of their dimensions in the x-y plane. The x-y plane is a plane generally parallel to the faces of the sanitary napkin 20. The term extensible includes articles that are stretchable and elastically stretchable (defined below). The sanitary napkin 20 shown in FIG. 4 is preferably extensible both in length and width. The sanitary napkin 20, in other embodiments however, may only be extensible in one of these directions. Preferably, the sanitary napkin 20 is extensible at least in the longitudinal direction.

The sanitary napkin 20 may in some preferred embodiments, in addition to being extensible, also be stretchable. The term "stretchable", as used herein, refers to articles that are extensible when stretching forces are applied to the article and offer some resistance to stretching.

More preferably still, the sanitary napkin 20 may be elastically stretchable. The terms "elastically stretchable" or "elastically extensible" are intended to be synonomous. These terms are illustrated in FIG. 4. These terms, used herein, mean that when the stretching forces designated "F" are removed, the sanitary napkin will tend to return toward its unextended or unstretched dimensions (or "original" dimensions) $L_U$ and $W_U$. The sanitary napkin 20 need not return all the way to its unstretched dimensions, however. It may, as shown in FIG. 4, return to relaxed dimensions (such as $L_R$ and $W_R$) between its unstretched dimensions and extended (or stretched dimensions) $L_S$ and $W_S$.

Making the sanitary napkin elastically stretchable will reduce the undesirable tendency of the sanitary napkin to gather longitudinally inward (i.e., bunch longitudinally) when forces which tend to stretch the sanitary napkin are removed. This is particularly true when the wearer's panties contract.

2. Extensibility of Preferred Sanitary Napkin Embodiments.

A. Introduction.

The sanitary napkin 20 can be in the form of many different embodiments.

These embodiments may be placed into at least four general categories for purposes of discussion. The first category deals with the type of forces used to extend the sanitary napkin. The first category is comprised of two sub-categories: (a) sanitary napkins that depend on manipulation by the user for their extensibility; and (b) sanitary napkins that need only be subjected to the typical forces encountered during use for their extensibility. Both types of sanitary napkins are within the scope of the present invention.

A second category is based upon whether or not an appreciable amount of force is required to extend the sanitary napkin. The sanitary napkin embodiments in the second category can be categorized as: (a) sanitary napkins that require some appreciable amount of force to extend; and (b) sanitary napkins that can be extended with very little force. Both types of sanitary napkins are within the scope of the present invention.

The third category relates to which components of the sanitary napkin are extensible. The sanitary napkin embodiments in the third category fall into two basic subcategories: (a) sanitary napkins that are comprised of all extensible components; and (b) sanitary napkins that are comprised of some extensible components and some inextensible components. Examples of sanitary napkins in the second sub-category include, but are not limited to: (i) sanitary napkins having an extensible backsheet with an inextensible topsheet and absorbent core; and (ii) sanitary napkins having an extensible topsheet and backsheet that form an extensible bag around an inextensible absorbent core.

The fourth category relates to whether the sanitary napkin is generally extensible, or is generally inextensible and is associated with some type of extensible element. The fourth category is comprised of at least two sub-categories: (a) sanitary napkins that are provided with extensible components; and (b) sanitary napkins adapted to extend by associating them with some type of extensible element. Examples of the second sub-category are sanitary napkins with extensible attachment elements. Again, both types of sanitary napkins are within the scope of the present invention.

The categories may encompass subject matter that overlaps into other categories. Other categories and subcategories exist as well. The overall extensibility characteristics are described below. It should be understood, however, that the overall extensibility characteristics will often depend on the sub-categories into which the sanitary napkin falls.

B. Extensibility Characteristics.

(1) Amount of Extensibility.

The sanitary napkin 20 is preferably capable of extending between about 110% to about 150% of its unextended length (and its unextended width). (That is, the sanitary napkin is capable extending between about 10 or 15% and about 50%.) More preferably, sanitary napkin 20 is capable of extending between about 120% to about 140% of its unextended length (and width). In other embodiments, the sanitary napkin 20 (or portions thereof) may be capable of extending greater or lesser amounts.

The amount of extensibility preferably corresponds to the amount the wearer's panties can stretch. In other words, during wear the sanitary napkin 20 preferably extends about the same amount as the wearer's panties. It has been found that 20% stretch is adequate to account for most stretch induced to the wearer's panties by body motions.

The forces required to extend the sanitary napkin and the other parameters associated with the extensibility of some preferred embodiments of the sanitary napkin 20 are summarized in the table in FIG. 8. The forces and other parameters in Table 1 (as noted above) are those associated with several preferred sanitary napkin embodiments.

It is to be understood that absorbent articles having parameters that fall outside of those shown in Table 1 may also fall within the scope of the present invention in some circumstances. It is also to be understood that all of the limits and ranges specified herein include all narrower ranges and limits that are within the specified limits and ranges. Thus, for example, if a range is specified as being between about 125% and about 150%, all narrower ranges, such as between about 130% and about 140%, and between about 130% and about 150%, etc., may be claimed even though these limits and ranges are not separately listed. The forces are measured in accordance with the Test Methods described in Section 5 of this description.

The table first provides values for the forces required to extend the sanitary napkin in the longitudinal direction. The sanitary napkin should preferably extend under the naturally occurring forces that cause the wearer's panties to stretch and move when the wearer moves. This will allow the sanitary napkin to stretch with the wearer's panties. The values in the table represent those forces.

The percentages of longitudinal extension provided above (and other measurements in Table 1) are measured along the longitudinal centerline L of the sanitary napkin 20. Some portions of the sanitary napkin 20 may, however, extend more (or develop a force wall after greater extension) than the portions of the sanitary napkin that lie along the longitudinal centerline L.

Figure 8A:
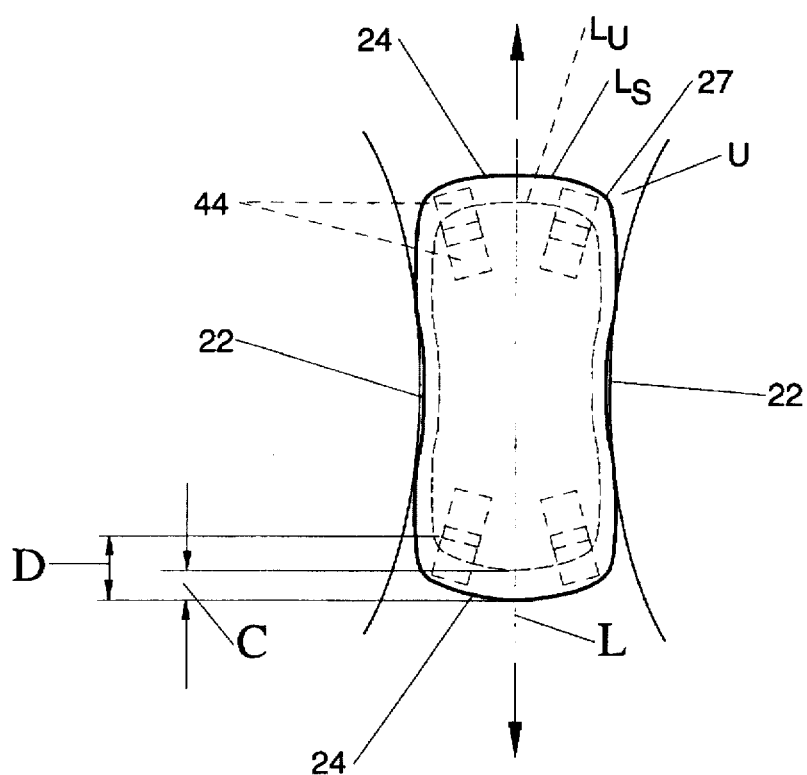
FIG. 8A is a plan view showing the extension of various portions of a sanitary napkin in a wearer's panties.

FIG. 8A shows that the portions of the sanitary napkin along the longitudinal edges 22 of the sanitary napkin 20 may extend more than the portions lying along the longitudinal centerline L. In this embodiment, the panty fasteners 44 on the garment-facing side of the sanitary napkin are affixed closely to the leg elastics of the wearer's panties, particularly in the corner regions 27. This greater extension occurs when the leg elastics of the wearer's panties stretch more than the portions of the panties underlying the longitudinal centerline of the sanitary napkin.

FIG. 8A shows that the portions of the sanitary napkin lying along the longitudinal centerline L extend a distance "C". The portions of the sanitary napkin 20 lying along the longitudinal side edges 22 extend a greater distance "D". These portions of the sanitary napkin 20 lying along the longitudinal side edges 22 may extend up to 175% –200% of their unextended length.

The table in FIG. 8 indicates that the sanitary napkin may also (or alternatively) be extensible in width. Further, FIG. 8 also indicates that the sanitary napkin may have an elastic "wall" (or "force wall") such that at a certain point, the forces required to further increase the length and/or width of the sanitary napkin greatly increase. These parameters are discussed more fully below.

The portions of the sanitary napkin which are capable of extending the amounts described herein, should preferably contain some absorbent material. The absorbent material is preferably capable of holding at least about 0.05 gram of liquid per square cm. This is measured by dipping the absorbent material into distilled water, removing the sample from the water, and allowing the sample to drip for 30 seconds. This absorbent material may be absorbent core material. Preferably, the absorbent material that is capable of extending comprises more than a single web of absorbent topsheet material.

An example of an embodiment which does not have absorbent material capable of extending is one in which the topsheet and backsheet extend (but are nonabsorbent), but the absorbent core does not. (Such an embodiment is not preferred because the extensible components do not include absorbent material. However, such a construction would still provide a degree of additional area coverage of the wearer's panties when extended.)

(2) Force to Extend

The set of figures in the second column of Table 1 are the amounts of force required to extend the sanitary napkin longitudinally. A set of figures is given for extending the sanitary napkin 25% and 40%.

The sanitary napkin will preferably extend at least 25% of its length under forces of less than or equal to about 800 grams, preferably less than or equal to about 400 grams, and most preferably less than or equal to about 300 grams.

The sanitary napkin will preferably extend about 40 percent of its length under forces of less than or equal to about 1250 grams. More preferably, the sanitary napkin will extend about 40 percent of its length under forces of less than or equal to about 800 grams. The sanitary napkin will (although not specified in Table 1) most preferably extend about 40 percent of its length under forces of less than or equal to about 600 grams.

The set of figures in the third column of the table are the amounts of force required to stretch the sanitary napkin across its width (in terms of the test described later which utilizes a 1.0 inch strip sample). The table is read in the same manner as for the longitudinal stretch.

The sanitary napkin 20 may be extensible only in length or width. The sanitary napkin need not be extensible both longitudinally and in width. T here are also some embodiments of the sanitary napkin of the present invention that may not fall within the ranges in the table. These embodiments of the sanitary napkin may still within the scope of the present invention even though they may fall outside some of the parameters set out in the table.

(3) Minimum Force to Extend

A minimum force to extend the sanitary napkin any appreciable distance (e.g., 5%, or more preferably 10%) is desired so that the sanitary napkin is easy to handle. A sanitary napkin with too low of a modulus of elasticity (that is, one that stretches too easily) is difficult for the user to handle and place into the panty. Such a sanitary napkin tends to become "stringy" similar to taffy.

Preferably, a force of at least about 50 grams is required for the sanitary napkin to extend about 25% and a force of at least about 100 grams is required to extend the sanitary napkin about 40%. In more preferred embodiments, a force of at least about 100 grams will be required to extend the sanitary napkin about 25%.

(4) Force Wall

Figure 9:
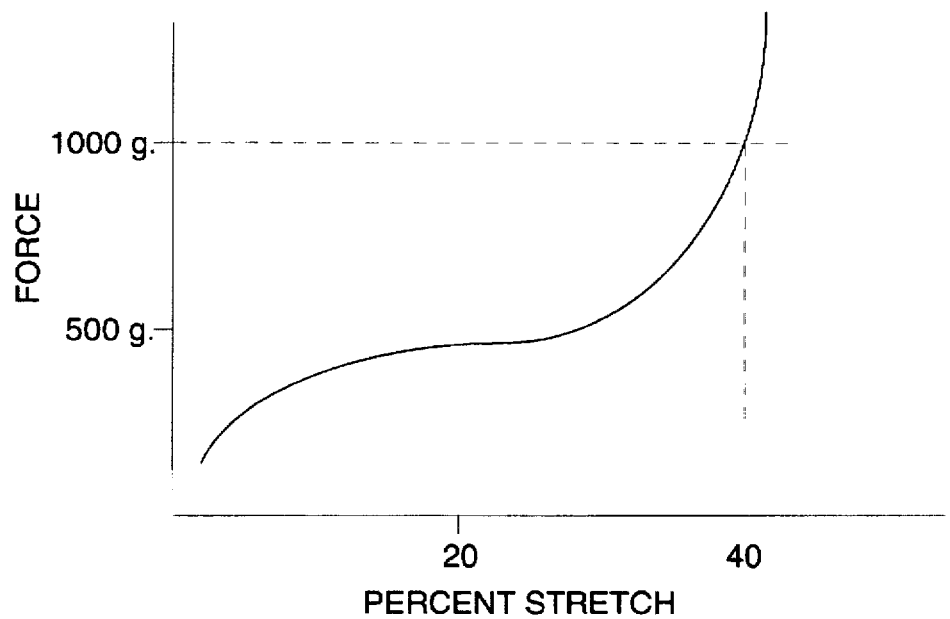
FIG. 9 is a graph which illustrates the forces required to stretch a sanitary napkin having a "force wall".

The sanitary napkin 20 preferably exhibits a stress-strain curve for longitudinal or lateral extension similar to that shown in FIG. 9.

The sanitary napkin preferably extends relatively easily up to a desired amount, then develops a force wall which prevents further extension under the forces normally encountered by the sanitary napkin during use and removal.

The sanitary napkin need not have a force wall in all embodiments. Further, in embodiments where a force wall is provided, the force wall may only be provided to prevent further increases in the length or width of the sanitary napkin.

Typically, it is more important to provide a force wall to prevent further increases in length. This is because the sanitary napkin may be subjected to the greatest stretching forces along its length.

The sanitary napkin is subjected to relatively large stretching forces in the longitudinal direction during removal of the napkin from the wearer's panties. A force wall prevents the sanitary napkin from stretching excessively during removal of the sanitary napkin from the wearer's panties. In addition, a force wall may be desirable since the length of the sanitary napkin is greater than its width, and, therefore, the sanitary napkin is capable of stretching a greater amount in the longitudinal direction than in the transverse direction.

Such a force wall may include, but is not limited to those which are intrinsic in the materials used in the components of the sanitary napkin 20 and those created as a result of its construction where mechanical "stops" are placed into the sanitary napkin to prevent extension beyond a certain point.

The first type of force wall can, for example, be seen in a hypothetical film. The film may produce a force wall when stretched to a certain limit. For instance, the film may extend about 10% (i.e., 110% of its original dimensions) before reaching a point where it cannot be stretched further without substantial force. Typically, however, the film will have to be subjected to forces in excess of those desired herein to achieve this initial 10% extension unless it is made extensible as described herein.

Figure 10:
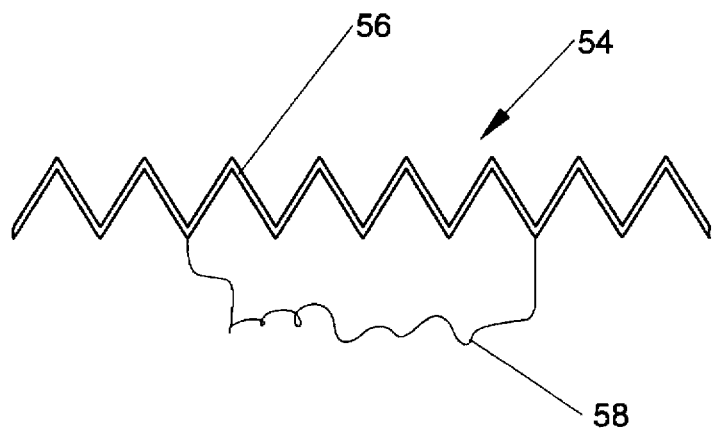
FIG. 10 is a schematic side view of a structure used to create force walls.

FIG. 10 shows an example of a mechanical "stop" 54. The schematic drawing depicts an extensible component 56. The extensible component 56 could, as a non-limiting example, comprise an extensible absorbent core or an extensible backsheet. The extensible component 56 has either an inextensible or less extensible restraining element 58 attached to it. The restraining element 58 is attached so that it is provided with slack or flaccid material which allows the core or backsheet to extend to a specified length, but no further without an appreciable amount of force.

Figure 11:
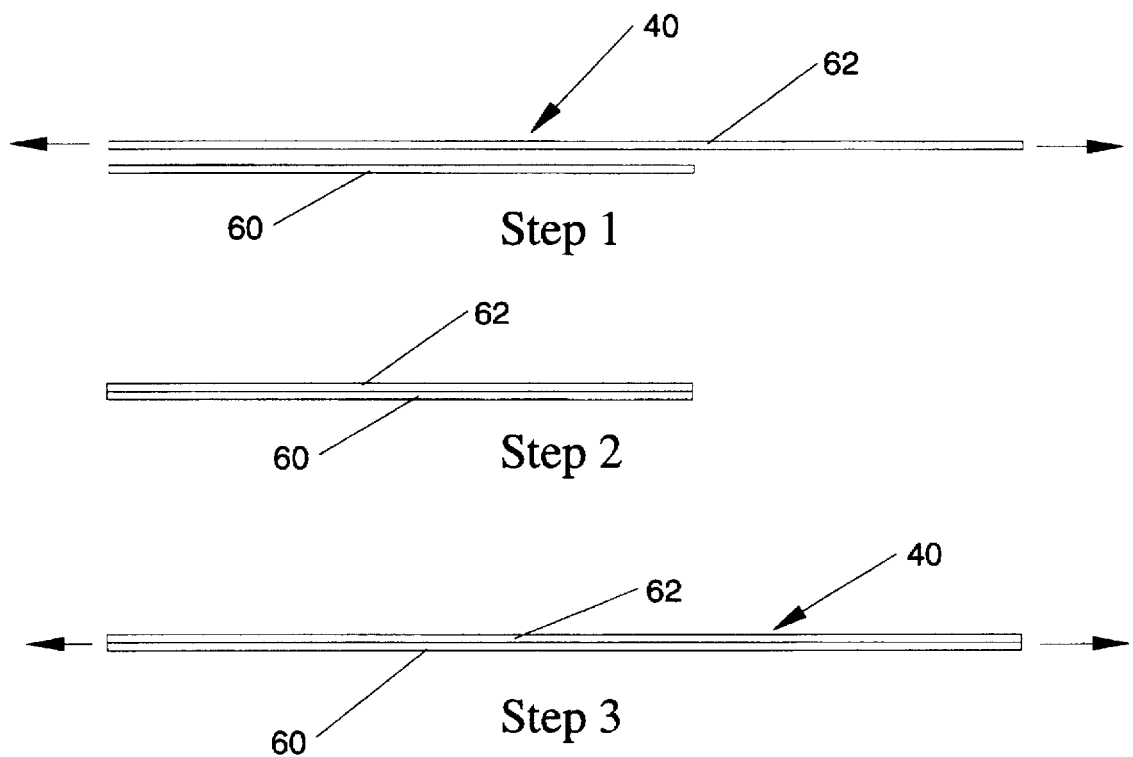
FIG. 11 is a schematic side view of another structure used to create force walls.

FIG. 11 shows an example of a laminate structure that can be used to provide the sanitary napkin with a stop or force wall. The example shown could represent the backsheet. The backsheet 40 could be a laminate comprised of a stretch laminate film, such as stretchable adhesive film 60 laminated to a pre-stretched polyethylene film 62. The two films are laminated together when the pre-stretched film 62 is relaxed. When the backsheet 40 is stretched, it will easily stretch up to the pre-stretched length of the polyethylene film 62, but will extend no further without substantial force.

The laminate structures that are used to provide the sanitary napkin with a stop or force wall need not be bonded across the entire interface between the component parts of the laminate.

For example, a laminate could be formed of a pre-stretched material, such as an elastic film and an absorbent material. The absorbent material could be intermittently bonded to the pre-stretched film when the film is in its stretched condition. The two components could be bonded at a plurality of lines, spots, or other locations. The components could be bonded by glue, thermal bonds, or any other suitable type of bond.

The resulting laminate will form puckered areas when it is relaxed. It can have unidirectional stretch, bi-directional stretch, or multi-directional stretch. The laminate will be able to extend to the pre-stretched dimensions of the elastic film, but will extend no farther without substantial force. The laminate thus formed could be used as a combination structure that serves as one or more of the basic components of the sanitary napkin.

(5) Amount of Recovery (or Percent Set)

The amount of recovery of the sanitary napkin can vary in different embodiments. Thus, upon extension to 125% or to 140% of its original length, the sanitary napkin need not return to its original length when the extending load is released. However, it is preferable if the sanitary napkin returns to less than 110% of its original length so that when the sanitary napkin extends, it will return as the panty material relaxes and/or the wearer's body moves, and will not bunch. Table 1 shows that in less preferred embodiments, the sanitary napkin may return to up to less than or equal to 125% of its original length when the extending load is released.

(6) Rate of recovery

If the sanitary napkin has the capability of recovering toward its unstretched dimensions, it preferably has a relatively low rate of recovery. A relatively low rate of recovery is desirable for several reasons.

The sanitary napkin will fit best against the wearer's body when it slowly returns toward its unextended dimensions after it is stretched. The sanitary napkin can be gently held against the wearer's body and in conformity therewith by the forces that tend to return the sanitary napkin toward its unextended dimensions. The sanitary napkin can also have regions that, due to creep of the same, may not tend to return toward their original dimensions. These regions may also aid body fit. Thus, the sanitary napkin can be contrasted with conventional elastic materials such as LYCRA that have substantial tendencies to retract.

A rapid recovery rate also makes the sanitary napkin undesirable from a consumer viewpoint in removing the sanitary napkin from the panty. After use, the user will often rip the sanitary napkin out of the crotch region of her panties in a fairly aggressive manner. If the rate of recovery is too high, the sanitary napkin may tend to snap back toward the user during removal (i.e., like a rubber band). This is particularly important when the longitudinal extension of the sanitary napkin is greater than or equal to about 20%.

The rate of recovery should be high enough, however, so the sanitary napkin will return to its recovered length or width within a few seconds (i.e., less than or equal to about 5 seconds).

Preferably, the sanitary napkin will return to its recovered length or width at a rate in the range of about 0.5 inches/sec. (about 1.3 cm./sec.) to about 2 inches/sec. (about 5 cm./sec.).

3. The Individual Components of the Sanitary Napkin.

The individual components which may be suitable for various embodiments of the sanitary napkin 20 of the present invention will now be looked at in greater detail with reference to FIGS. 1–3.

A. The Topsheet (1) General Characteristics of Preferred Topsheet Materials.

The topsheet 38 comprises a first liquid pervious component. When the sanitary napkin 20 is in use, the topsheet 38 is in close proximity to the skin of the user. The topsheet 38 is preferably as compliant, soft feeling, and non-irritating to the user's skin as possible. The topsheet 38 should further exhibit good strikethrough and a reduced tendency to rewet, permitting bodily discharges to rapidly penetrate it and flow toward the core 42, but not allowing such discharges to flow back through the topsheet 38 to the skin of the wearer.

The topsheet 38 has two sides (or faces or surfaces), including a body-facing side 38A and a garment-facing side (or core-facing side) 38B. The body-facing side 38A of the topsheet 38 generally forms at least a portion of the body-contacting surface ("body surface") 20A of the sanitary napkin 20. The topsheet 38 has two longitudinal edges 38C and two end edges 38D.

(A similar numbering system will be used for the other components of the sanitary napkin. That is, the side of the component facing the wearer's body will be designated by the number of the component and a reference letter "A". The side facing the wearer's undergarments will be designated by the number of the component and the letter "B". The side and end edges will be designated by the number of the component and the reference letters "C" and "D" respectively.)

A suitable topsheet 38 may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims.

Suitable woven and nonwoven materials can be comprised of natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers) or from a combination of natural and synthetic fibers.

When the topsheet 38 comprises a nonwoven web, the web may be spunbonded, carded, wet-laid, meltblown, hydroentangled, combinations of the above, or the like.

Apertured films are generally preferred for the topsheet 38 because they are pervious to liquids and, if properly apertured, have a reduced tendency to allow liquids to pass back through and rewet the wearer's skin. Suitable apertured films can be made of any of the materials specified in the publications that describe films and methods of making films which are incorporated by reference herein.

Suitable films are described in U.S. Pat. No. 3,929,135 issued to Thompson on Dec. 30, 1975, U.S. Pat. No. 4,324,426 issued to Mullane et al. on Apr. 13, 1982, U.S. Pat. No. 4,342,314 issued to Radel et al. on Aug. 3, 1982, U.S. Pat. No. 4,463,045 issued to Ahr, et al. on Jul. 31, 1984, and U.S. Pat. No. 5,006,394 issued to Baird on Apr. 9, 1991. Additional suitable formed and hydro-formed films are described in U.S. Pat. Nos. 4,609,518, 4,629,643, 4,695,422, 4,772,444, 4,778,644, and 4,839,216 issued to Curro, et al., and in U.S. Pat. No. 4,637,819 issued to Ouellette, et al.

Still other materials suitable for use as a topsheet are described in U.S. Pat. No. 4,775,579 issued to Hagy, et al. on Oct. 4, 1988, U.S. Pat. No. 4,798,604 issued to Carter on Jan. 17, 1989, U.S. Pat. No. 5,023,124 issued to Kobayashi on Jun. 11, 1991, and in European Patent Application 0 304 617 A2 published Mar. 1, 1989 in the name of Suda, et al.

In still other embodiments, the materials described in some of the above references (such as the stretchable polymeric materials described in U.S. Pat. No. 4,798,604 issued to Carter) could be made into the films described in other references. For instance, the stretchable polymeric materials described in U.S. Pat. No. 4,798,604 could be made into the macroscopically expanded three dimensional plastic film having a substantially non-glossy surface described in U.S. Pat. No. 4,463,045.

Figure 12:
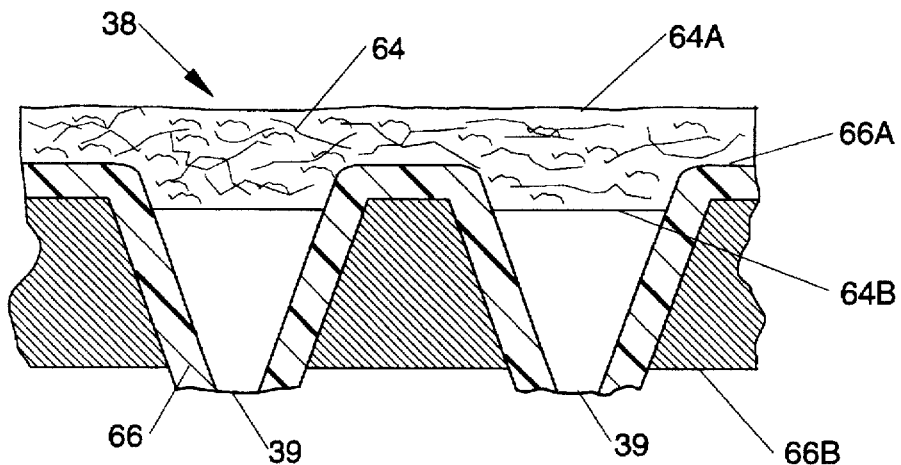
FIG. 12 is an edge view of an alternative topsheet that comprises a nonwoven material and an apertured film.

In another embodiment shown in FIG. 12, the topsheet 38 could comprise a structure comprising a nonwoven material or fabric 64 and an apertured film such as three dimensional apertured plastic film 66. The nonwoven material provides the topsheet with an improved, less plastic-like feel.

In one preferred version of the embodiment shown in FIG. 12, the nonwoven material 64 has a basis weight from about 1 to about 40 g/sq. m., more preferably from about 8 to about 12 g/sq. m. One preferred nonwoven material comprises a carded thermally dot bonded polypropylene web. Some preferred nonwoven fabrics are manufactured by the Fiberweb Group of Simpsonville, S.C. under the trademarks CELESTRA and HOLMESTRA.

The plastic film 66 is a thermoplastic material provided with a multiplicity of tapered capillaries 39 in a manner, size, configuration, and orientation set forth in U.S. Pat. No. 3,939,135 issued to Thompson. The film is treated with a surfactant such as ATMER 645 manufactured by ICI Specialty Chemicals. Preferably, the surfactant is incorporated into the polyolefin resin pellets from which the film is made.

The nonwoven fabric 64 and the apertured plastic film 66 may be integrally formed into a composite structure such as that shown in FIG. 12 by embedding the fibers of the nonwoven material into the thermoplastic film when the latter is in a molten condition using a vacuum lamination process. Such a topsheet is described in greater detail in U.S. patent application Ser. No. 07/794,745 filed by Aziz, et al. on Nov. 19, 1991. In alternative embodiments, the nonwoven fabric and the film may be placed into a face-to-face relationship. The two components are preferably secured to each other in these latter embodiments. Suitable methods for securing the two components include, but are not limited to adhesives, fusion including heat bonding and/or pressure bonding, ultrasonics, and dynamic mechanical bonding.

Figure 13:
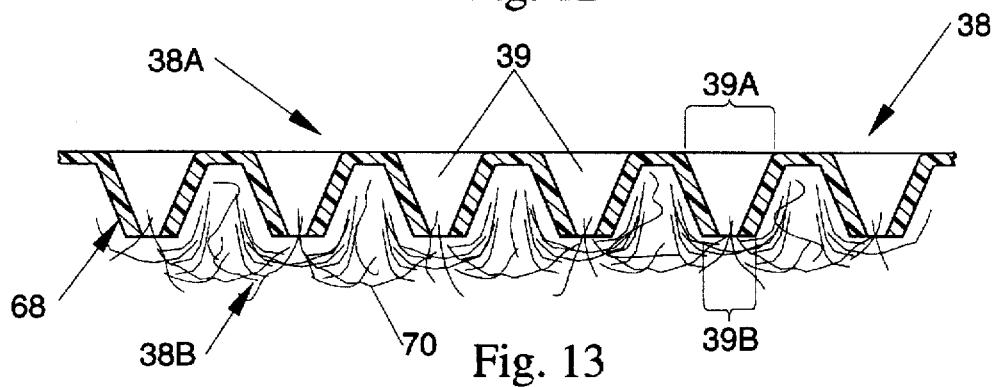
FIG. 13 is a simplified schematic view of a topsheet material that comprises an apertured film with entangled nonwoven fibers.

FIG. 13 shows that in still other embodiments, the topsheet 38 may comprise a fiber-entangled film. The term "fiber-entangled film" refers to apertured films having fibers entangled in and around their apertures.

The apertured film 68 of such a topsheet could comprise any of the films or scrims described herein. One particularly suitable apertured film 68 for use in such a topsheet is disclosed in U.S. Pat. No. 4,463,045 and ring-rolled (as described below) to provide it with a degree of extensibility. The film 68 can be ring rolled before or after the entanglement of the fibers.

The film 68 has nonwoven fibers 70 loosely mechanically or thermo-mechanically entangled therewith. The fibers 70 are preferably entangled along or from the direction of either the body-facing side 38A, or the core-facing side 38B.

The fibers 70 could be mechanically or thermo-mechanically entangled with the film 68 by any suitable process. For instance, the fibers 70 could be meltblown onto the film, spunbonded onto the film, carded onto the film, thermo-mechanically entangled with the film such as being flocked or meltblown on the plastic film while the film is still in its molten state, or hydro-entangled with the film. One suitable meltblowing process is disclosed in Exxon U.S. Pat. No. 3,978,185 issued to Buntin, et al.

The fibers 70 may be either hydrophilic or hydrophobic. Suitable hydrophilic fibers may be formed from intrinsically wettable fibers such as nylon co-polymers comprising a nylon component and a hydrophilizing component. Such a material is commercially available from Allied Signal Inc. under the trade designation Hydrofil SCFX.

In a preferred embodiment, the fibers 70 are of a thermoplastic synthetic nature. Suitable polyethylene fibers are available from the Dow Chemical Company under the trade designation ASPUN, and polypropylene fibers are available from the Exxon Corporation under the trade name ESCORENE 3,400 and 3,500 series.

Once formed, the fiber-entangled film structure is preferably treated by any known methods to render it hydrophilic. Such process will allow the apertures 39 of the film to better handle liquids. The composite structure may be ring-rolled after these treatment processes.

The fiber-entangled topsheet 38 material provides more intimate contact between the apertured film 68 and the nonwoven fibers 70. This can create advantages of improved liquid transport through the film 68 to the fibers 70 and the underlying layers. It may also provide improved comfort if the fibers lie along the body-facing side 38A of the topsheet 38. It can also provide improved comfort when fibers lie along the core-facing side 38B of the topsheet 38 since the film 68 portion of the topsheet 38 will be less likely to separate from the underlying entangled fibers 70 and move into the crevices of the wearer's body.

(2) Alternative Ways of Providing the Topsheet With Extensibility.

There are several basic ways of providing the topsheet materials described above with extensibility. A non-limiting number of these ways are described below.

One way of making the topsheet 38 extensible is by performing a mechanical operation, such as pleating, corrugating, or ring rolling on the topsheet material to provide folds in the topsheet that are able to open when the topsheet is stretched. Such a process can be performed on many of the topsheet materials described above.

In one preferred embodiment of the present invention, the topsheet 38 is made in accordance with U.S. Pat. No. 4,463,045 and ring rolled to provide it with a degree of longitudinal extensibility.

Such a topsheet is described in the following patent applications which were filed on Jul. 23, 1991: U.S. patent application Ser. No. 07/734,404 filed in the names of Thompson, et al.; U.S. patent application Ser. No. 07/734,392 filed in the names of Thompson, et al.; and, U.S. patent application Ser. No. 07/734,405 filed in the names of Buenger, et al. These patent applications may be referred to collectively as the "Capillary Channel Fiber" patent applications.

Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 filed by Gerald M. Weber et al. on Feb. 28, 1991, U.S. patent application Ser. No. 07/662,537 filed by Kenneth B. Buell et al. on Feb. 28, 1991, and U.S. patent application Ser. No. 07/662,543 filed by Gerald M. Weber et al. on Feb. 28, 1991 (collectively referred to herein as the "Ring Rolling" patent applications).

The fold lines in the corrugations of a ring rolled topsheet should run in the transverse direction so the topsheet is longitudinally extensible. In other embodiments, the fold lines could run in the longitudinal direction, both directions, and/or other directions. The topsheet 38 will be extensible in directions perpendicular to the fold lines.

Figure 14:
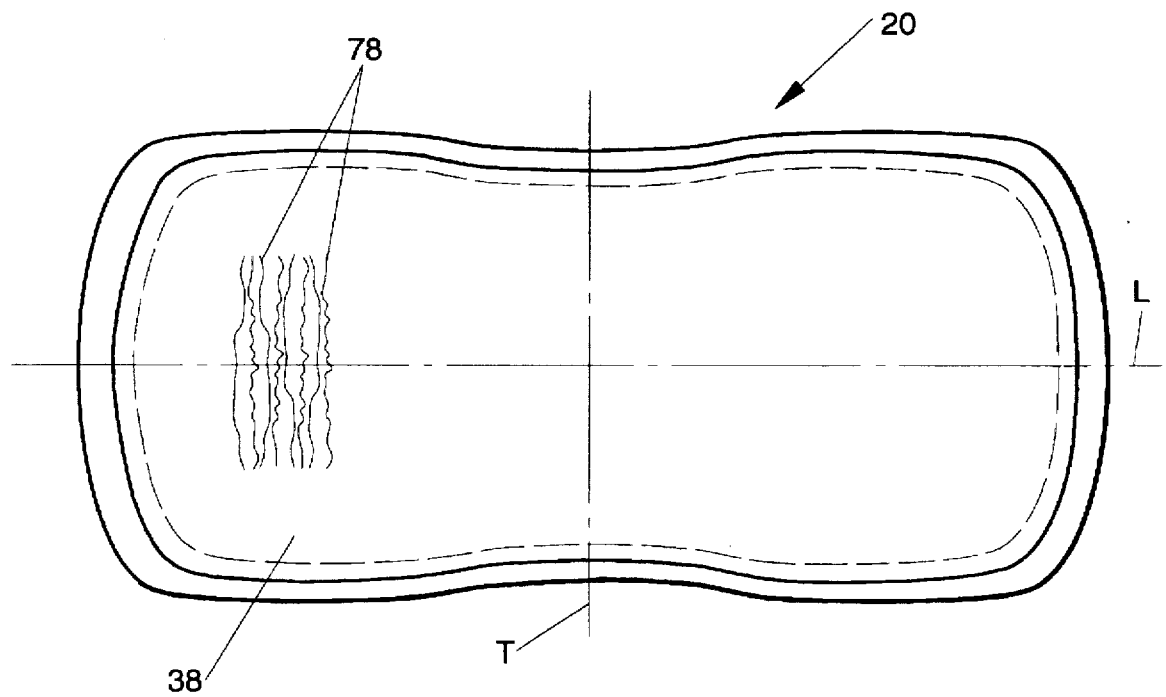
FIG. 14 is a top plan view of a sanitary napkin having a topsheet comprised of a nonwoven web with fibers generally oriented in the transverse direction (only a portion of which are shown).

FIG. 14 shows that in other embodiments, the topsheet 38 could be comprised of a nonwoven material having fibers 78 generally oriented in a direction perpendicular to the direction of the desired stretch. The topsheet, for instance, could be comprised of fibers generally oriented in the transverse direction to provide extensibility in the longitudinal direction.

Figure 15:
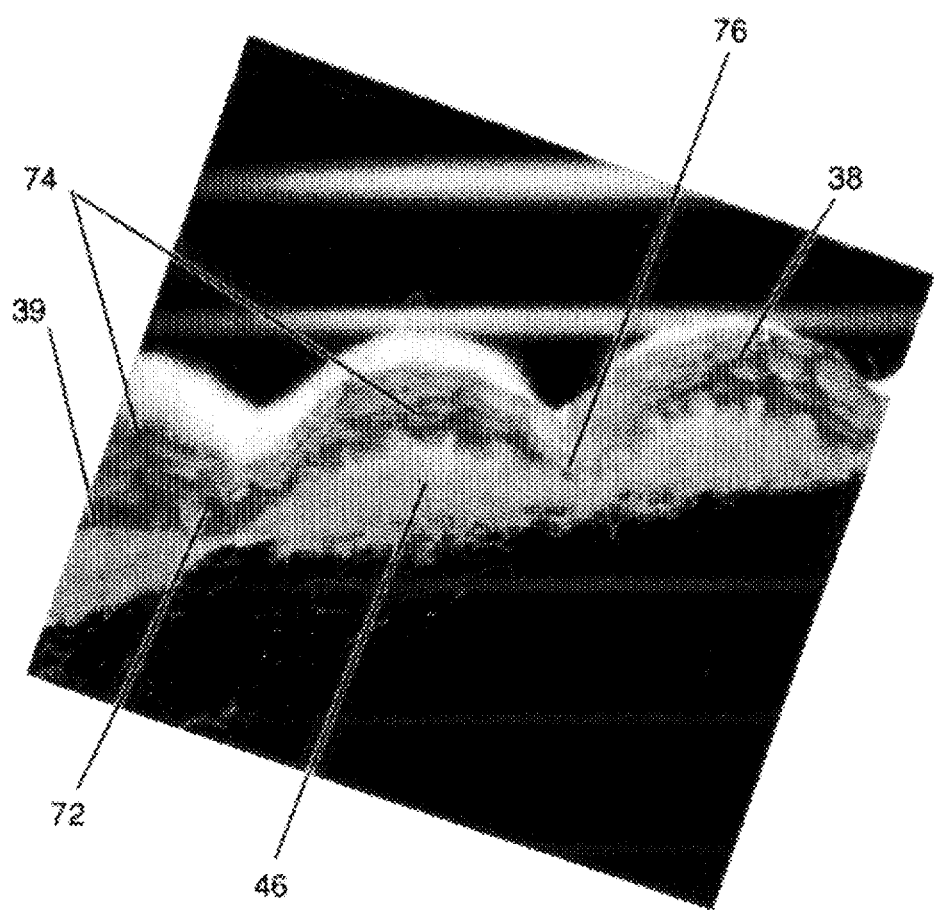
FIG. 15 is a photograph showing a cross-sectional view of an embodiment on which an underlying fibrous layer has been stretched and bonded to an apertured film.

FIG. 15 shows another alternative topsheet embodiment. In FIG. 15, the topsheet 38 is bonded to an underlying acquisition layer 46 by the type of individual fusion bonds 72 shown in FIG. 5. In the embodiment shown in FIG. 15, the acquisition layer 46 is stretched before it is fused to the topsheet 38. The topsheet 38 and acquisition layer 46, thus, form a laminate. When the stretched laminate is relaxed, the laminate has tufted areas 74 formed therein between bonded areas 72 and valleys 76 formed at the bonds.

The embodiment shown in FIG. 15 provides a key advantage. It (and its various alternative embodiments) allows a stretchable laminate to be formed from materials that are not ordinarily thought of as being stretchable. The apertured plastic film topsheet 38, for instance, is not normally thought of as being extensible. However, the topsheet 38 is provided with a degree of extensibility when it is secured to a layer such as the acquisition layer 46 after the acquisition layer 46 has been extended and the two component materials are thereafter relaxed.

The tufted areas 74 in such a laminate can also provide certain benefits. The tufted areas 74 are typically soft. They will also place the absorptive fibers of the acquisition layer 46 closer to the wearer's body than the nontufted bonded areas. This construction may also enhance absorption (particularly at the tufted areas 74).

In other alternative embodiments, both the topsheet 38 and the acquisition layer 46 can be stretched prior to fusing the same together.

In other embodiments, the topsheet 38 can be made extensible by forming it from extensible, or more preferably, stretchable materials. The topsheet 38 can, for instance, be an apertured film made of a polyethylene/Kraton blend such as Exxon film EXX-7 available from the Exxon Corporation. This will yield a stretchable material without any mechanical manipulation.

In other embodiments, the topsheet materials tan include low basis weight nonwovens (nonwoven materials having a basis weight from about 18 to about 25 grams per square meter). An example of such a nonwoven material is manufactured by Veratec, Inc., a Division of International Paper Company, of Walpole, Mass. under the designation P-8.

In other embodiments, the topsheet could be comprised of a thermo-formed mass of fibers or hydroentangled nonwovens.

Figure 16:
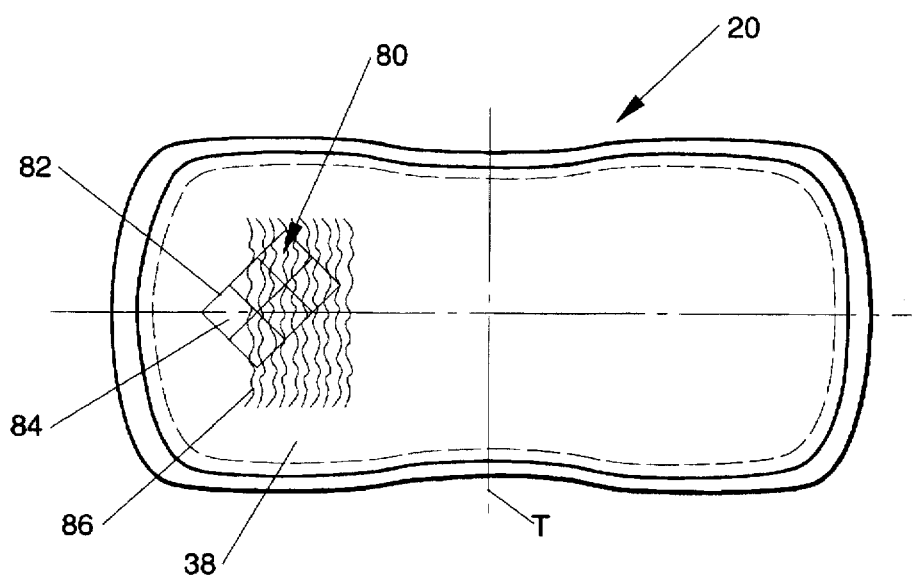
FIG. 16 is a top plan view of a sanitary napkin having a topsheet comprising an elastic scrim with fibers entangled with the scrim. (The scrim is shown on a greatly enlarged scale, and only a portion of the scrim is shown.)

FIG. 16 shows that in still other embodiments, the topsheet 38 could have elastic structural components. One example of such a structure is a net, screen, or scrim 80 comprised of elastic ribs 82. An example of such a structure is disclosed in U.S. Pat. No. 4,062,995 issued to Korpman Dec. 13, 1977. The net could have square-shaped or diamond-shaped apertures 84 between its ribs. Such a structure is generally stretchable in all directions. Elastic or inelastic fibers 86 could be added or adhered to the net.

The topsheet 38 can, in still other alternative embodiments, be manufactured into a structure that is capable of stretching in more than one direction from materials that are only capable of stretching in one direction.

Figure 17:
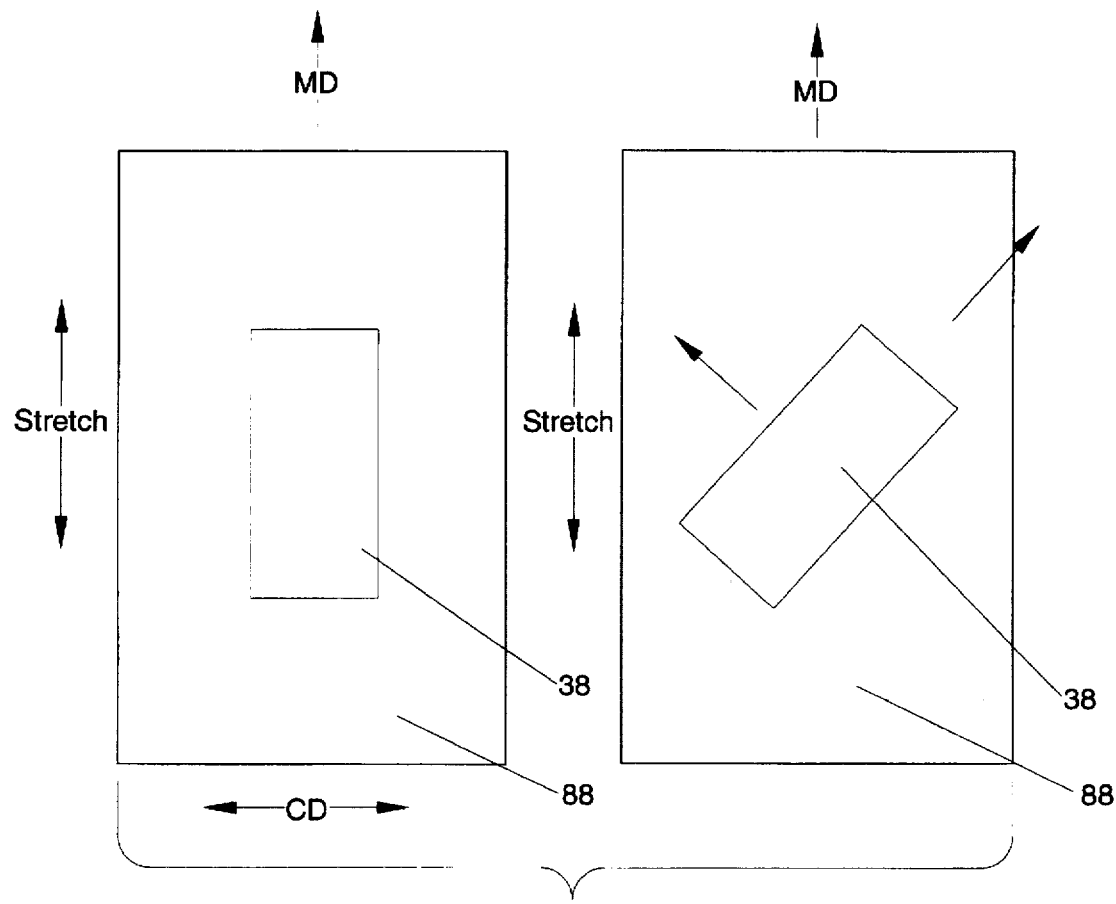
FIG. 17 shows a conventional process that could be used to cut a web of stretchable material into individual topsheets, and a process for creating a multi-directional stretch topsheet by cutting the web of stretchable material fed into the process at an angle (or on a "bias" to the machine direction).

FIG. 17 shows an example of a process that can be used for this purpose. The left side of FIG. 17 shows a conventional process that could be used for cutting a web of stretchable material 88 into individual topsheets 38. The web 88 runs in the machine direction (MD). This is also the direction the web 88 stretches.

The right side of FIG. 17 shows a process of creating a multi-directional stretch topsheet by cutting the web of stretchable material at an angle (or on a "bias" to the machine direction). In a variation of this process, the web could be fed in at an angle and cut in the same direction as shown in the conventional process. The resulting cut topsheet 38 will be able to stretch in two directions as shown by the arrows near the cut topsheets.

Figure 17A:
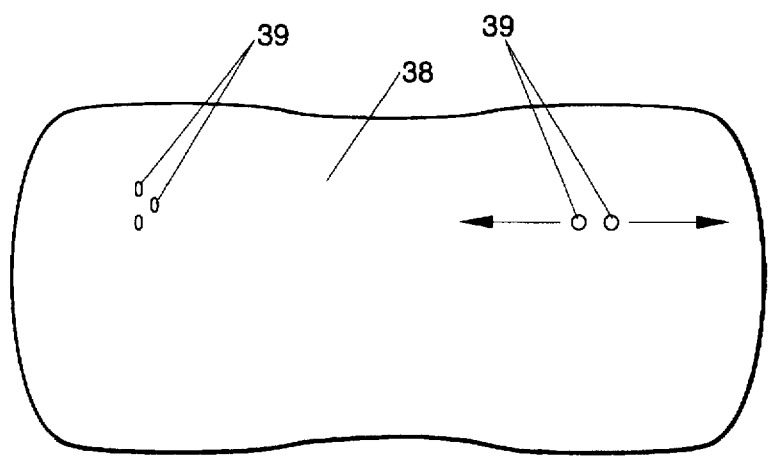
FIG. 17A is a plan view of a film topsheet for a sanitary napkin that has apertures that may provide the topsheet with extensibility.

FIG. 17A shows that in still other embodiments, an apertured film topsheet 38 can be provided with apertures 39 having a geometry that is conducive to allowing the topsheet 38 to stretch in a particular direction.

In still other embodiments, the topsheet 38 could be slit for extensibility as described below for the absorbent core.

Figure 17B:
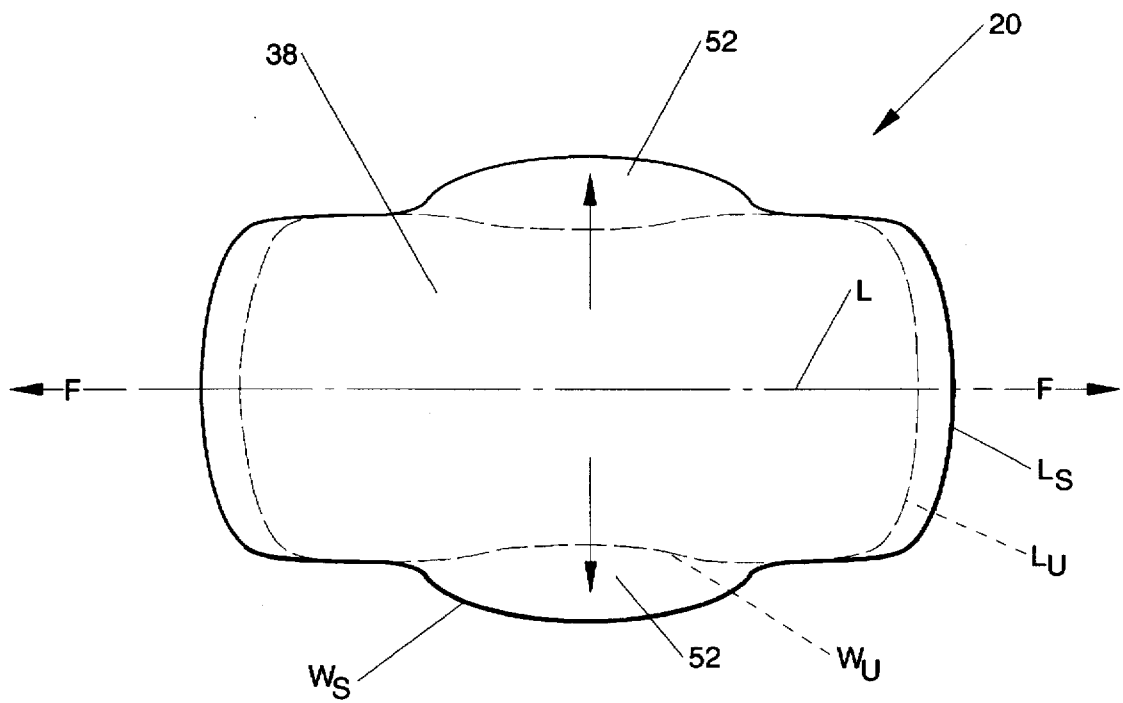
FIG. 17B is a schematic plan view of a reversibly necked topsheet material.

In still other embodiments (shown in FIG. 17B), the topsheet 38 can comprise a reversibly necked material. Reversibly necked materials generally comprise materials that increase in width (rather than decrease) when extended longitudinally. Such materials are useful in sanitary napkins because they are not subject to the reduction in their ability to cover a given area of the crotch of the wearer's panties when the sanitary napkin is stretched. In fact, their ability to cover the crotch area will increase when they are stretched. As shown in FIG. 17B, if this increase in width is great enough, these materials can be used to form flap-like structures when the sanitary napkin is stretched.

One suitable way of creating a reversibly necked material is described in U.S. Pat. No. 4,965,122 issued Oct. 23, 1990 to Morman.

(3) Additional Steps.

In addition to the above, in preferred embodiments of the present invention, at least a portion of the topsheet 38 is treated with a surfactant. This can be accomplished by any of the common techniques well known to those skilled in the art.

Suitable methods for treating the topsheet 38 with a surfactant are described in a number of references, including U.S. Pat. Nos. 4,950,264 and 5,009,653 issued to Osborn, and in U.S. patent application Ser. No. 07/794,745 filed by Aziz, et al. on Nov. 19, 1991. The latter patent application teaches treating the apertured film component of a nonwoven/apertured thermoplastic formed film topsheet with a surfactant. The surfactant is preferably incorporated into the resin used to make the thermoplastic formed film.

Treating the topsheet 38 with a surfactant renders the topsheet 38 more hydrophilic. This results in liquid penetrating the topsheet 38 faster than it would if the surface were not treated. This diminishes the likelihood that body fluids will flow off topsheet 38 rather than being drained through the topsheet 38.

In addition, in preferred embodiments, the inner surface 38B of topsheet 38 is secured in contacting relation with an underlying absorbent layer. This contacting relationship results in liquid penetrating topsheet 38 faster than if the topsheet 38 were not in contact an absorbent component. However, it is not absolutely necessary to bond the face of the topsheet 38 to the face of the underlying layer.

The topsheet 38 can be maintained in contact with an underlying absorbent component by applying adhesives between the topsheet and the underlying component, by entangling the fibers of the underlying layer with the topsheet, by fusing the topsheet 38 to an underlying absorbent layer by a plurality of discrete individual fusion bonds, or by any means known in the art.

Figure 5:
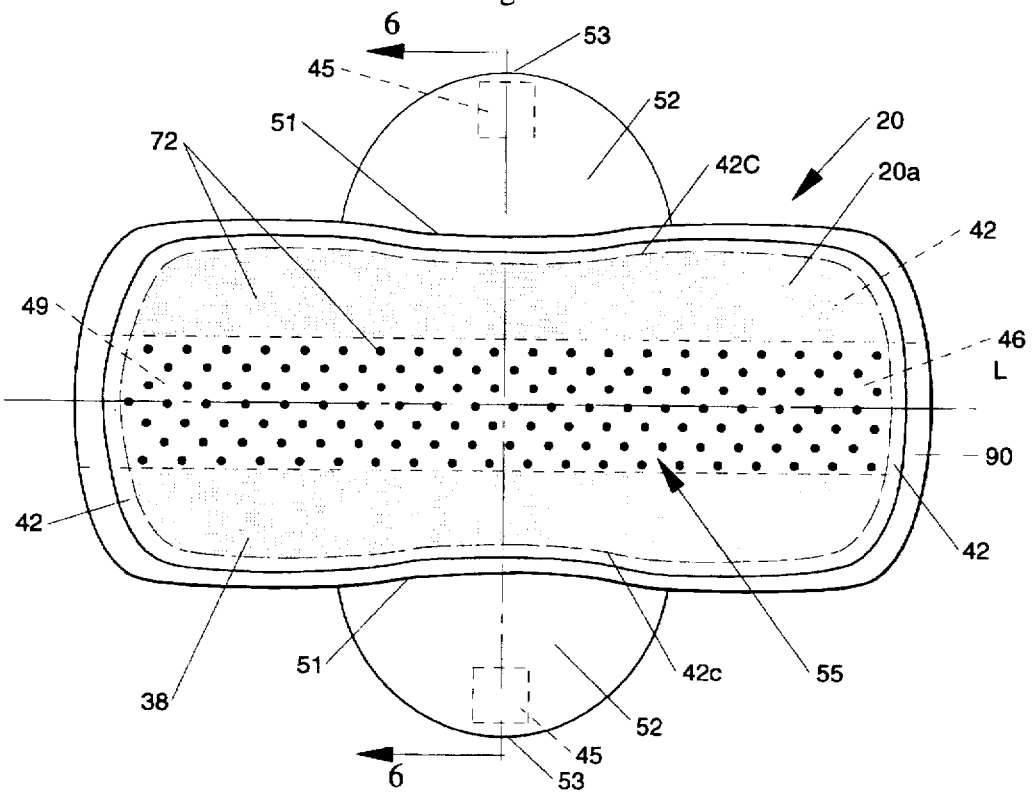
FIG. 5 is a top plan view of a stretchable sanitary napkin which has optional side flaps and a topsheet fusion bonded to an underlying component.
Figure 7:
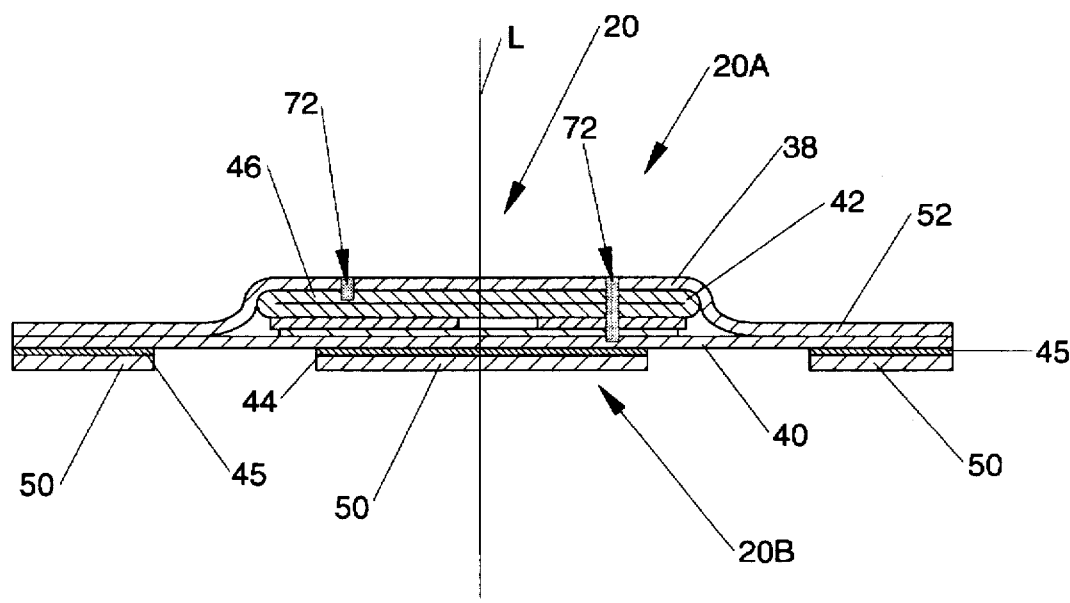
FIG. 7 is a simplified transverse cross-sectional view similar to that of FIG. 6, showing an alternate arrangement of the components of the sanitary napkin.

FIGS. 5 and 7 show a preferred type of fusion bond which forms bonded areas which provide structures with drainage passageways for liquids to pass through to the underlying absorbent material. These preferred fusion bonds are described in greater detail in U.S. patent application Ser. No. 07/810,774 filed in the names of Cree, et al. on Dec. 17, 1991.

B. The Absorbent Core (1) General Characteristics of Preferred Absorbent Core Structures.

The absorbent core 42 is positioned between the topsheet 38 and the backsheet 40. The absorbent core 42 provides the means for absorbing menses and other body fluids.

The absorbent core 42 need not have an absorbent capacity much greater than the total amount of fluid anticipated to be absorbed. The absorbent core 42 is generally compressible, conformable, and non-irritating to the user's skin. It can comprise any material used in the art for such purpose. Non-limiting examples include natural materials such as comminuted wood pulp which is generally referred to as airfelt, creped cellulose wadding, hydrogel-forming polymer gelling agents, modified cross-linked cellulose fibers (described below), capillary channel fibers, absorbent foams, absorbent sponges, synthetic staple fibers, polymeric fibers, peat moss, or any equivalent material or combinations of materials.

The polymeric gelling agents listed above may also be referred to as "absorbent gelling materials" or "superabsorbent materials". Polymeric gelling agents are those materials which, upon contact with liquids such as water or other body liquids, imbibe such liquids and thereby form hydrogels. In this manner, liquids discharged into the absorbent core 42 can be acquired and held by the polymeric gelling agent, thereby providing the articles herein with enhanced absorbent capacity and/or improved liquid retention performance.

The polymeric gelling agent which is employed in the absorbent core 42 will generally comprise particles 41 of a substantially water-insoluble, slightly cross-linked, partially neutralized, hydrogel-forming polymer material. The term "particles", as used herein, can refer to particles in any form, such as in the form of pellets, flakes, or fibers.

The general characteristics of one basic type of absorbent core 42 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent, the disclosures of which are all incorporated by reference herein. (The absorbent cores 42 described herein need not include superabsorbent material particles, however.)

Suitable cross-linked cellulose fibers for the absorbent core are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,898,642, issued Feb. 6, 1990 to Moore, et al.; and U.S. Pat. No. 4,935,022 issued Jun. 19, 1990 to Lash et al.; EPO Patent Application Publication Nos. 0 427 316 A2 and 0 427 317 A2 published in the name of Herron, et al. on May 15, 1991; and EPO Patent Application Publication No. 0 429 112 A2 published in the name of Herron, et al. on May 29, 1991.

Suitable capillary channel fibers (that is, fibers having channels formed therein, preferably, on their exterior surfaces) for the absorbent core are described in greater detail in the Examples provided below, in EPO Patent Application 0 391,814 published Oct. 10, 1990, and in the aforementioned Capillary Channel Fiber patent applications.

Suitable absorbent cores comprising foams are described in U.S. patent application Ser. Nos. 07/743,839, 07/743,950, 07/743,947, and 07/830,159 (P&G Case Nos. 4451, 4452, 4453, and 4453R) The first, third and fourth applications listed were filed in the names of DesMarais, et al. The second application listed was filed in the name of Young, et al. The first three applications were filed on Aug. 12, 1991, and the fourth on Feb. 12, 1992. Additional cores comprising foams are described in European Patent Application 0 293 208 B1.

Absorbent cores comprising sponges are described in U.S. Pats. Nos. 3,512,530, 3,954,493 and French Patent 2,203, 827.

Additional suitable absorbent cores that can be provided with extensibility are described in the following references: U.S. Pat. No. 4,773,903 and 4,865,596 issued to Weisman, et al. on Sep. 27, 1988 and Sep. 12, 1989, respectively. These patents disclose composite absorbent structures comprising webs of entangled blown microfibers, substantially nonabsorbent crimped staple fibers, particles of hydrogel-forming polymeric gelling agents and a hydrophilizing agent.

Other suitable absorbent core materials comprise mixtures of melt blown elastic fibers and absorbent materials. One such core material comprises a hydro-entangled composite of cotton and melt blown fibers known as product #7102-102 available from Fiberweb of Simpsonville, S.C. In other embodiments, the cotton could be replaced with other absorbent materials such as FSA fiber Type 101 or 102 available from Courtaulds Fibers, Ltd. West Midlands, England. Alternatively, two plies of a material such as the above product #7102-102 could be laminated together with a particulate polymeric gelling agent in between and provided with extensibility to produce a highly absorbent extensible laminate.

In addition, the absorbent core 42 can be comprised of many materials described herein as being suitable for use as topsheets. In order to be suitable, however, these materials must be absorbent or used in conjunction with some absorbent material. For instance, the absorbent core 42 could be comprised of a structure similar to the elastic scrim shown in FIG. 16 with absorbent fibers adhered thereto.

(2) Providing the Absorbent Core With Extensibility.

There are many possible extensible absorbent core embodiments. These include, but are not limited to the embodiments described below. The components of the embodiments described below can also be combined in any suitable manner to form additional embodiments.

(a) Laminates

In one preferred embodiment shown in FIG. 2, the absorbent core 42 is a laminate. The laminate is comprised of a layer of superabsorbent polymer material, such as in the form of particles 41, disposed between two air-laid tissues, first and second tissue layers (or "upper" and "lower" tissue layers) 43 and 47, respectively.

The first and second tissue layers 43 and 47 provide containment of the superabsorbent polymer material, improve lateral wicking of the absorbed exudates throughout the absorbent core 42 and provide a degree of absorbency. The tissue layers 43 and 47 can be comprised of a single tissue web which is folded with the superabsorbent material particles 41 between, or two separate sheets of the same (or different) tissue.

A suitable laminate is a superabsorbent laminate known as WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, issued to Pedersen et al. on Aug. 21, 1984, U.S. Pat. No. 4,260,443, issued to Lindsay et al. on Apr. 7, 1981, and U.S. Pat. No. 4,578,068 issued to Kramer, et al. on Mar. 25, 1986.

The laminate absorbent core 42 can be made extensible by making the same from tissue paper having between 20% and 200% stretch (i.e., capable of extending between about 120% and 300% of its original length). Such tissue sheets can be made by a number of processes. The tissue paper may in one embodiment, be conventionally creped tissue. For example, the tissue paper may be a BOUNTY tissue that is run through a creping process.

In other embodiments, the tissue may be made by a suitable variation of the process described in U.S. Pat. No. 4,191,609 issued to Trokhan on Mar. 4, 1980, or by a suitable variation of the processes described in U.S. Pat. No. 4,529,480 issued to Trokhan on Jul. 16, 1985, or the processes described in European Patent Application Publication Nos. WO 92/00414, WO 92/00415, and WO 92/00416 published Jan. 9, 1992. In the latter cases, the tissue may be made extensible by one or more of the following procedures: adjusting the angle of the doctor blade to provide additional creping; tailoring the characteristics of the paper's network region to allow a certain amount of stretch; or, by removing the paper web from the Yankee dryer earlier than ordinary before it is subjected to further drying to give it a creped effect.

In alternative embodiments, a tissue with no or very low initial crepe can be creped after lamination. The creping process in this case could occur by passing the laminate through two matched rolls such that they would yield a corrugated laminate tissue with stretch in the range of 20% to 200% (capable of extending between about 120% and 300% of its original length). The corrugations should be perpendicular to the direction of desired stretch.

In a related alternative embodiment, the laminate could be creped by adhering the laminate to a surface and creping the laminate off the surface. This could be done in a manner similar to the step of removing the paper web from a Yankee dryer described in the aforementioned EPO patent applications.

In another related embodiment, the laminate could be creped by pressing a pattern into it while the laminate is on a flat surface. For instance, a pair of flat plates could be used to impress a pattern into the laminate similar to that shown in U.S. Pat. No. 4,578,068 issued to Kramer, et al.

Figure 18:
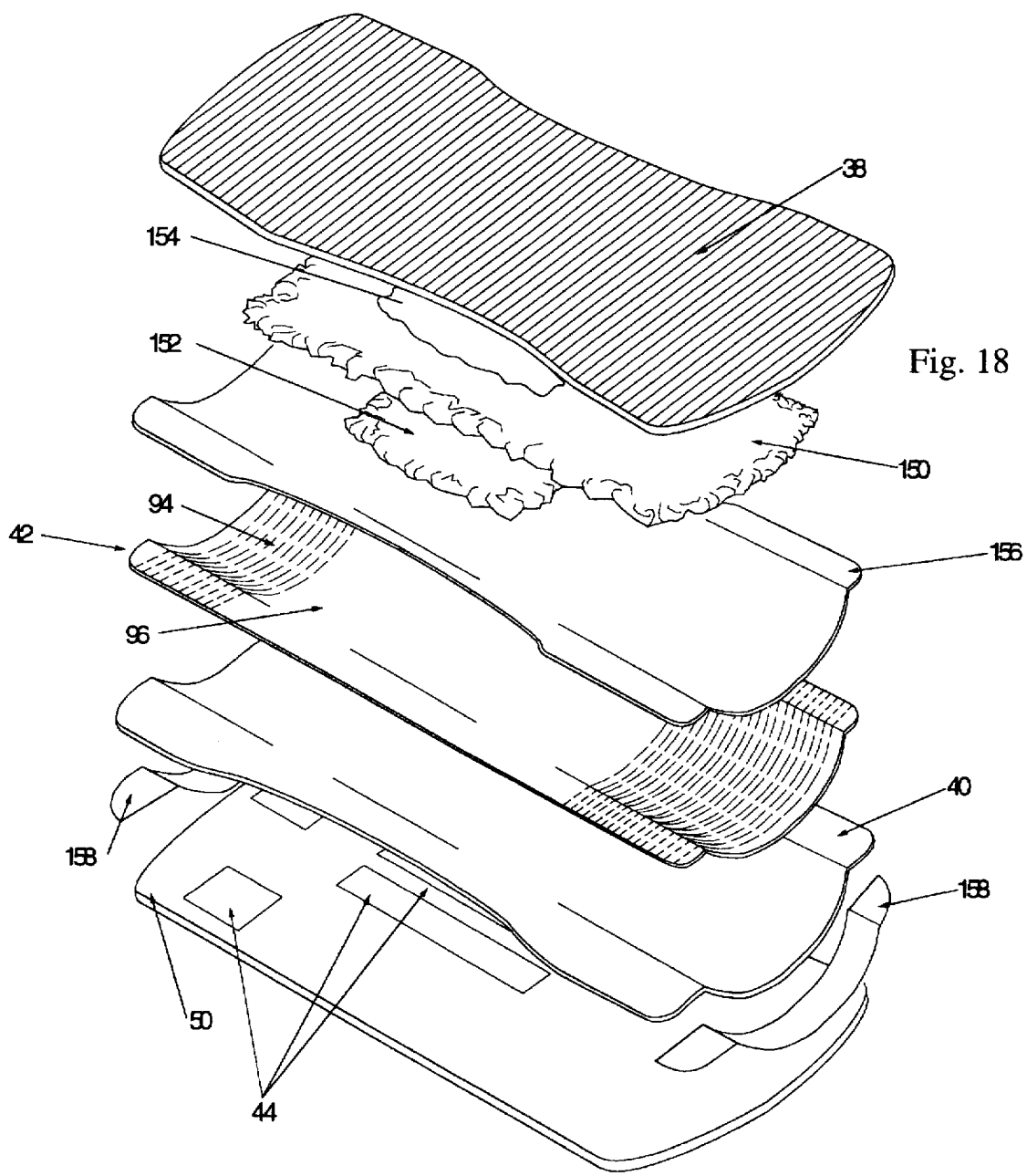
FIG. 18 is an exploded perspective view showing the assembly of a stretchable sanitary napkin provided with a slit absorbent core.
Figure 18A:
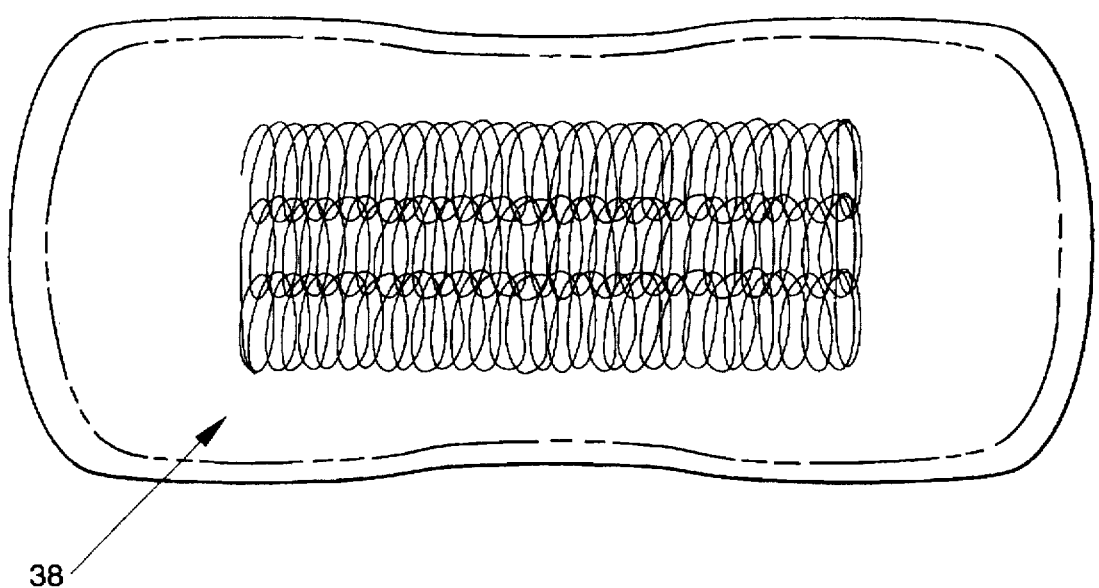
FIG. 18A is a plan view showing a preferred glue pattern applied to the underside of the topsheet of the sanitary napkin shown in FIG. 18.
Figure 19:
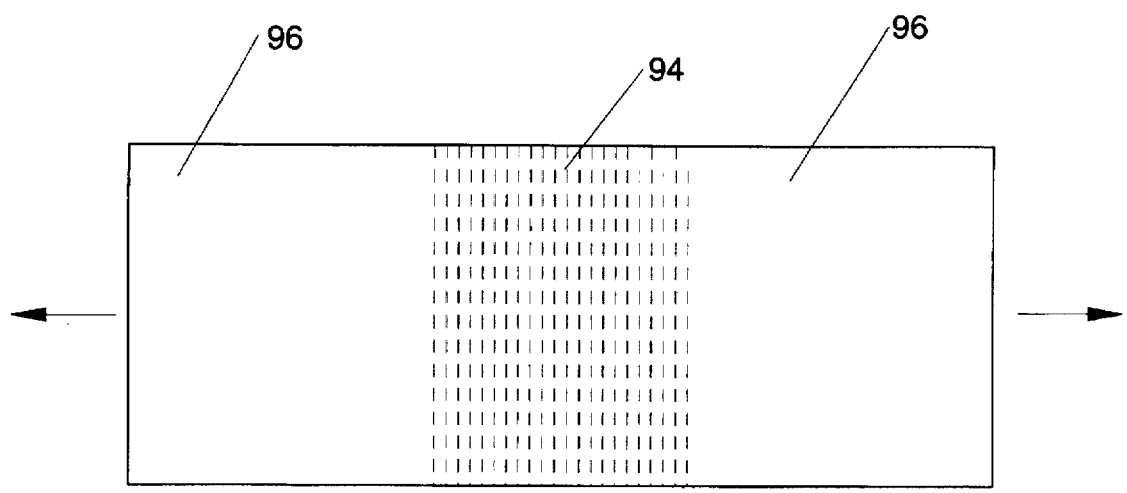
FIG. 19 is a plan view of an absorbent core slit in the middle and not at the ends.
Figure 20:
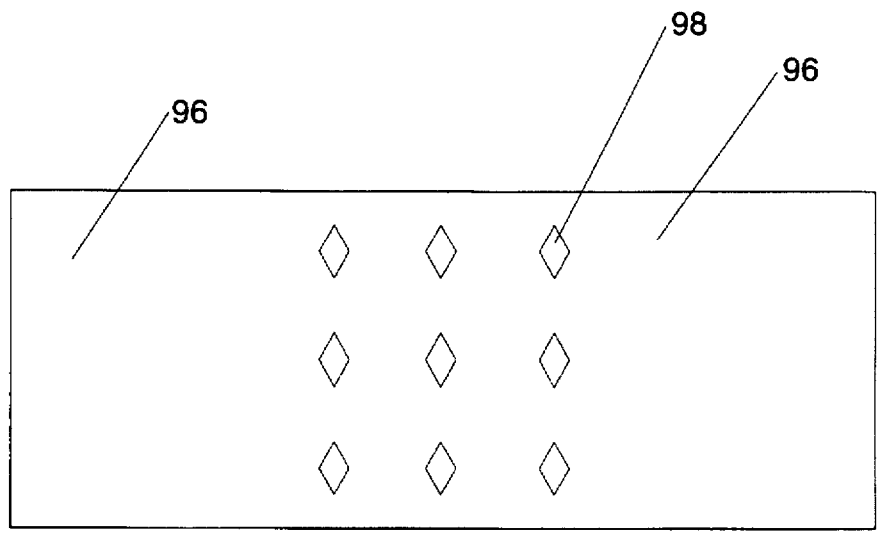
FIG. 20 is a plan view of an absorbent core provided with diamond-shaped apertures.

In alternative embodiments, the laminate can be cut or slit to provide an extensible absorbent core structure. FIG. 18 shows that in a particularly preferred embodiment, the absorbent core 42 is a laminate as described above which is slitted or partially slitted for longitudinal extensibility. FIG. 19 shows an alternate absorbent core that is slit at the central region, and not at the end regions. FIG. 20 shows an alternate absorbent core that has diamond-shaped apertures cut therein. Any other suitable shape or shapes of apertures can be used.

Other types of slit absorbent materials are described in European Patent Application Publication Number 0 293 208 B1 published by Lion Corporation on Jul. 24, 1991.

The longitudinal and end edges 22 and 24 of the sanitary napkin 20 are preferably sealed to prevent the wicking and expulsion of liquid or liquid-containing superabsorbent material from the napkin when it is extended. Alternatively, the edges 42C and 42D of the absorbent core 42 may be sealed rather than sealing the edges of the entire sanitary napkin. The edges of the core 42 may, for example, be wrapped or covered by a tissue layer. In other alternative embodiments, the edges of the tissue may be folded, or otherwise manipulated to prevent the wicking and expulsion of liquid or liquid-containing superabsorbent material particles 41 from the core 42. All permanent seals around the perimeter of the sanitary napkin 20 should not break upon lengthening (i.e., any seal is intended to remain for the duration of the use of the sanitary napkin.)

In any of the laminate absorbent core embodiments described above, a sheet of other any other known absorbent materials including, but not limited to peat moss, modified cross-linked cellulose fibers, or synthetic fibers could replace the cellulose fibers in one or more of the tissue layers. The basis weights of the tissue layers could also be varied between layers.

(b) Structures Containing Mixtures of Absorbent Materials and Superabsorbent Materials.

The absorbent core 42 could, instead of comprising a laminate structure, be comprised of a mixture of the absorbent materials and superabsorbent materials described above.

For example, mixtures of superabsorbent materials with airfelt, modified cross-linked cellulose fibers cross-linked carboxy methyl cellulose such as that described in U.S. Pat. No. 4,475,911 issued to Gellert on Oct. 9, 1984, peat moss, or other absorbent materials can be used to make thin webs. These thin webs may then be creped, ring-rolled, slit, or otherwise manipulated as described herein to produce an extensible absorbent core 42.

The superabsorbent material particles 41 can be distributed in any known manner in any of the embodiments described herein. The superabsorbent material particles 41 may be homogeneously blended with the absorbent materials described herein. In other embodiments, the superabsorbent material particles can be distributed in a superabsorbent material concentration gradient in the sanitary napkin. Known manners for establishing such a concentration gradient are described in European Patent Application No. 0 198 683 published Oct. 22, 1986 in the name of Duenk, et al., U.S. Pat. No. 4,699,823 issued Oct. 13, 1987 to Kellenberger, et al. and U.S. Pat. No. 5,009,650 issued to Bernardin on Apr. 23, 1991.

(c) Structures Containing Mixtures of Various Types of Fibers.

The absorbent core 42 can comprise a mixture of various types of natural or synthetic fibers and particular superabsorbent materials.

(i) The "Blended" Core.

Figure 21:
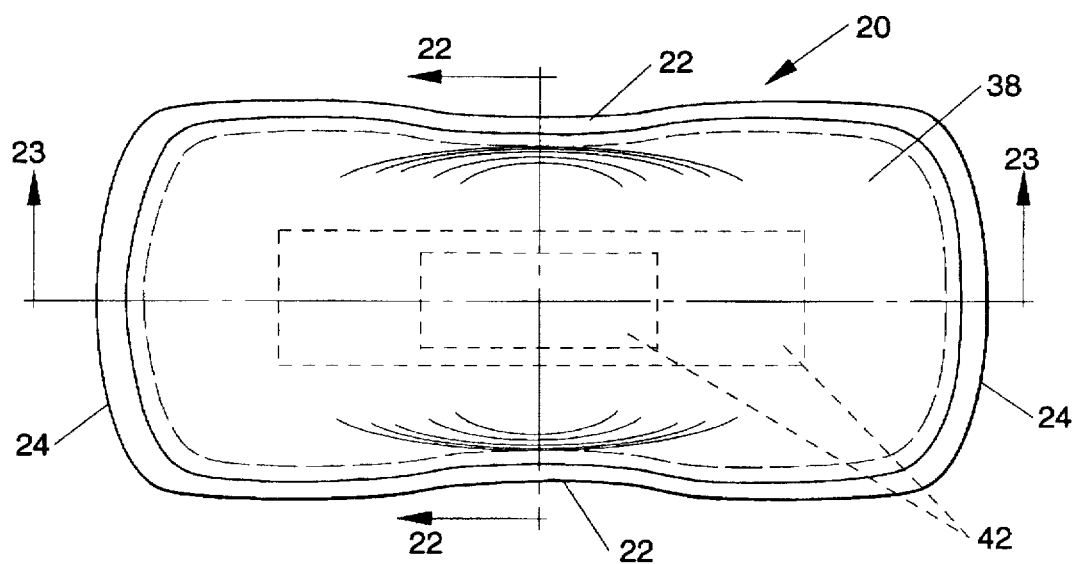
FIG. 21 is a top plan view of a thick sanitary napkin having a blended core and a profiled shape.
Figure 22:
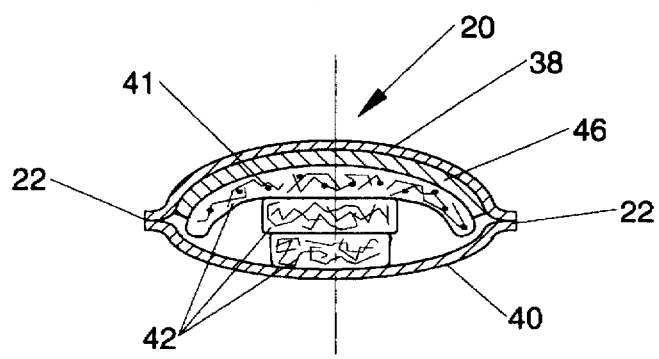
FIG. 22 is a simplified cross-sectional view taken along line 22—22 of FIG. 21.
Figure 23:
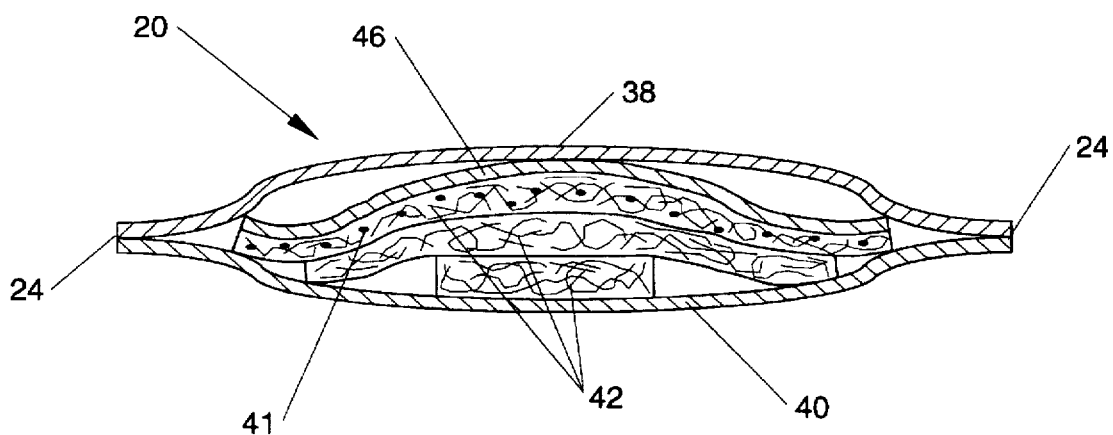
FIG. 23 is a simplified cross-sectional view taken along line 23—23 of FIG. 21.

FIGS. 21–23 show one particularly preferred absorbent core 42 that will be referred to as a "blended" core. This particular core arrangement is shown in a relatively thick sanitary napkin 20. It can, however, also be formed into a thin web for use in thin products.

The blended absorbent core 42 comprises a batt of fibers, preferably in the form of a homogeneous blend of fibers. The blended core 42 is comprised of at least two groups (or types) of fibers. These include a first group (or type) of low denier, relatively short, hydrophilic fibers, and from about 5% to about 90% of higher denier (and is preferably about 10%), longer synthetic fibers that comprise a second group (or type) of fibers. The blend ratio of the two groups of fibers can be varied to produce the properties desired for different types of absorbent articles. (All percentages specified in this description are by weight unless stated otherwise.)

The first group of fibers can comprise natural fibers such as cotton, cellulose, or other natural fibers. The first group of fibers can alternatively or additionally comprise synthetic fibers such as superabsorbent material fibers and capillary channel fibers, mechanically or chemically modified natural fibers, including but not limited to, rayon, chemical thermal mechanical pulp (or "CTMP" or "TMP"), ground wood, or cross-linked cellulose fibers. For one embodiment, the first group of fibers comprises airfelt. The fibers in the first group of fibers are either inherently hydrophilic, or they may be rendered hydrophilic by treating them in any of the manners described previously to render them hydrophilic.

Performance is improved by selecting a relatively stiff fiber which maintains a substantial portion of its compression resistance when wetted. (That is, the fibers should have a high compressive modulus.) Preferably, the fibers selected are both compression resistant and wet and dry resilient (i.e., they tend to both resist compression and to spring back when compressed). Cross-linked cellulose fibers are especially preferred for these criteria. (It is understood, however, that cross-linked cellulose fibers are sufficiently modified that they may no longer be considered as either cellulosic, or as natural fibers, per se.)

The second group of fibers should also be of high compressive modulus and should maintain a relatively high modulus when wetted. The second group of fibers should also preferably be wet and dry resilient. Suitable fibers include, but are not limited to synthetic fibers comprised of any of those materials specified below as being suitable for use as the fibers of the acquisition layer 46. (Fiber lengths, denier, etc. are, however, not necessarily the same. Some preferred fiber lengths, etc. are described below.)

The fibers in the second group of fibers are preferably longer than the fibers in the first group of fibers. Preferably, the fibers in the second group of fibers are greater than or equal to about ¼ inch (about 0.6 cm.) long, and are more preferably greater than or equal to about ½ inch (about 1.3 cm.) long. The denier of the fibers in the second group of fibers are preferably greater than the denier of the fibers in the first group of fibers. The fibers in the second group of fibers preferably have a denier per filament of between about 6 and about 40. More preferably, the denier is between about 15 and about 30, and most preferably between about 15 and about 25.

The fibers in the second group of fibers may be hydrophilic, hydrophobic, or partially hydrophilic and partially hydrophobic. The fibers in the second group of fibers preferably have at least some hydrophilic component (preferably a cellulosic component). The fibers in the second group of fibers can be provided with a hydrophilic component in a number of suitable ways. These include, but are not limited to coating or treating the fibers to render them, or at least their surfaces, hydrophilic.

Suitable synthetic fibers are available from Eastman Kodak Textile Fibers Division Kingsport, TN as the KODEL 200 and 400 Series. One suitable type of synthetic fiber is the KODEL 410 fiber.

One particularly suitable type of synthetic fibers for use in the second group of fibers are crimped polyester fibers. A suitable polyester fiber is the KODEL 431 fiber. These KODEL fibers are preferably crimped at a crimping frequency of between about 5 and 7, preferably about 6, more preferably 6.3 crimps per linear inch (i.e., per 2.5 cm.). The fibers are preferably crimped at a crimping angle of between about 70° to about 91°, preferably about 88°. Crimping provides the fibers with improved resilience, among other desired properties. The fibers have a denier of 15 per filament and a length of about 0.5 inch (about 1.3 cm.). They may be coated with a hydrophilic or hydrophobic finish by any suitable method known in the art.

In an alternative embodiment, it is possible to replace the cellulose fibers in the first group of fibers with very short, low denier, synthetic fibers (with hydrophilic surfaces). The blended core 42 in this situation would consist of short, low denier, hydrophilic first group of synthetic fibers (such as polyester fibers coated with a proprietary permanently wettable finish known as CELWET) and long, high denier second group of synthetic fibers. Polyester fibers coated with CELWET are available from the Hoechst Celanese Corporation of Charlotte, N.C.

Such a blended core may also contain particles of hydrogel-forming polymer gelling agents to increase the absorptive capacity of the core.

In one preferred embodiment, the hydrogel-forming polymer gelling agents comprise "high-speed" absorbent gelling materials. The term "high-speed" absorbent gelling materials, as used herein, means those absorbent gelling materials that are capable of absorbing exudates at such a rate that they reach at least about 40%, preferably at least about 50%, and most preferably at least about 90% of their capacity in less than or equal to about 10 seconds.

A suitable method for measuring the percent rate of capacity is described in U.S. patent application Ser. Nos. 07/637,090 and 07/637,571 filed respectively by Noel, et al. and Feist, et al. In alternative embodiments, it is also possible for the high-speed absorbent gelling materials to be mixed with other types (or ordinary speed) absorbent gelling materials.

Preferably, in the embodiment described immediately above, the high-speed absorbent gelling materials are in fibrous form. Fibrous superabsorbent materials (though not necessarily fibrous high-speed absorbent gelling materials) are discussed more fully in U.S. Pat. No. 4,855,179, issued Aug. 8, 1989, to Bourland, et al.

The term "fibrous absorbent gelling materials", as used herein, is intended to include absorbent gelling materials in the form of fibers that are comprised entirely of absorbent gelling material and bi-component fibers that are comprised at least partially of other materials which have their surfaces coated with absorbent gelling materials. A suitable fibrous high speed absorbent gelling material is known as FIBERSORB SA7000 formerly manufactured by Arco Chemical Company of Newton Square, Pennsylvania. Other suitable fibrous high speed superabsorbent fibers are the polyacrylate-based fibers known as FSA fiber Type 101,102, 111, or 112 available from Courtlauds Fibers, Ltd.

The effective utilization of hydrogel-forming polymer gelling agents is believed to be improved in such a blended core. The use of higher concentrations of hydrogel-forming polymer gelling agents may also be possible.

The blended absorbent core 42 is preferably compressed to a density of at least about 1.5 g/cubic inch (about 0.09 g/cm$^3$). The blended core 42 may be compressed to densities at least as high as about 4.0 g/cubic inch (about 0.25 g/cm$^3$) to improve fluid wicking while still maintaining good softness and flexibility. (The density values specified above do not include the weight of any particles of absorbent gelling material.) Densification may be applied to the entire absorbent core 42 or only to selected portions. Patterned densification allows tailoring of the fluid handling properties to a specific need. For example, the density may be very low in the fluid target area to maximize fluid acquisition speed, and density may be very high near the core edges to maximize fluid wicking.

In one particularly preferred embodiment, the improved absorbent core 42 is an air-laid blend comprised of approximately 15% of 0.5 inch long, 15 denier per filament crimped polyester fibers and approximately 85% of cross-linked cellulose fibers compressed to a density of about 1 g/cubic inch (about 0.06 g/cm$^3$).

The blended absorbent core 42 can be used as the entire core or it can be used as one or more layers in a layered construction. The blended absorbent core 42 can be used with or without an acquisition layer.

FIGS. 21-23 show an example of a core 42 in which layers of core material are used to produce a "profiled" sanitary napkin 20. The profiled sanitary napkin 20 is thicker in the center of the sanitary napkin and tapers so it becomes thinner toward the edges 22 and 24. FIGS. 22 and 23 show that such a profiled sanitary napkin 20 can be made by stacking layers having relatively large length and width dimensions on top of those with smaller length and widths (or vice versa).

In a layered construction, one or more layers can consist of all cellulose or cellulose/hydrogel-forming polymer material blends. The layers could also have differing fiber and/or absorbent gelling material content or composition. For example, a higher percentage of absorbent gelling material could be provided in the lower layers to provide additional liquid storage capacity.

In other embodiments, elastic fibers may be included in the second group of fibers. Suitable elastic fibers include melt blown fibers, such as those included in the hydroentangled melt blown fiber and cotton composite known as product #7102-102 available from Fiberweb, or fibers made of a polyethylene/Kraton blend, such as the material used to make Exxon film EXX-7.

(ii) Other Types of Cores.

Other core structures that provide extensible properties include unbonded nonwoven structures of synthetic fibers or various woven structures.

For instance, nonwoven structures including fibrous superabsorbent materials such as Fibersorb can be combined with various synthetic fibers to produce absorbent cores. These nonwoven structures can be made extensible by utilizing various patterns of bonding and fiber lay down.

The stretch properties of these nonwoven structures can be enhanced by any of the different methods described herein. Suitable methods for enhancing the extensibility of stretch include, but are not limited to ring rolling, including elastic fibers within the core, and including fibers that are crimped or curled that are capable of being extended (such as those shown in FIGS. 58 and 59) for extensibility.

One suitable structure comprises the aforementioned melt blown elastic fibers and cotton Fiberweb product #7102-102 with superabsorbent material. The superabsorbent material could be in either particulate or fibrous form. In other alternative embodiments, the structure could contain modified cross-linked cellulose fibers. The cross-linked cellulose fibers could be added to the unbonded elastic fibers and superabsorbent material. In other embodiments, the cross-linked fibers could replace the elastic fibers (if the cross-linked fibers are intrinsically extensible), or the superabsorbent material.

(3) Providing the Core with Elasticity.

The absorbent core 42 may be made not only extensible, but elastically extensible in any of the embodiments described in this specification.

The absorbent core 42 may be made elastically extensible even though it has no elastic properties of its own. The absorbent core 42 can be made elastically extensible by attaching it to an elastic backsheet or topsheet so that the absorbent core 42 will extend and retract with the elastic topsheet or backsheet.

The sanitary napkin (or other absorbent article) 20 could also include any additional absorbent layers or other components such as are described in the patents incorporated by reference. For example, the absorbent article may comprise an acquisition layer or patch of cross-linked cellulose fibers positioned between the topsheet 38 and the absorbent core 42.

C. The Backsheet (1) General Characteristics of Preferred Backsheet Materials.

The backsheet 40 is impervious to liquids and, thus, prevents body fluids from soiling the clothing of the user. A suitable backsheet 40 may be manufactured from a wide range of materials. Suitable materials include embossed or nonembossed polyethylene films and laminated tissue.

Suitable polyethylene film are manufactured by Monsanto Chemical Corporation and marketed in the trade as Film No. 8020, by Clopay Corporation of Cincinnati, Ohio under the designation P18-0401, and by Tredegar Film Products of Terre Haute, Ind. under the designation XP-39385.

In one alternative embodiment of the sanitary napkin 20 (typically in which the topsheet 38 overlays only the main body portion 21 and does not extend out to form the top surface of the flaps, if any), the backsheet 40 may be comprised of two layers. In such a case, the backsheet 40 may comprise a first layer of lofted material disposed on the core-facing side 40A of the backsheet. The purpose of the first layer is to provide a comfortable, non-irritating surface against the body of the wearer.

The lofted layer may be comprised of any suitable material, such as a nonwoven material. Preferably, the lofted layer comprises a hydrophobic nonwoven material.

The second layer may be disposed on the garment side 40B of the backsheet 40, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 40 may also be made of a soft, cloth-like material which is hydrophobic relative to the topsheet 38. A polyester or polyolefinic fiber backsheet 40 has been found to work well. A particularly preferred soft, cloth-like backsheet 40 material is a laminate of a polyester nonwoven material and a film such as described in U.S. Pat. No. 4,476,180 issued to Wnuk on Oct. 9, 1984.

(2) Providing the Backsheet With Extensibility.

There are many possible types of extensible backsheets. These include, but are not limited to the embodiments described below.

Generally, many of the techniques described above for providing the topsheet with extensibility may also be used to create an extensible backsheet 40. Thus, the backsheet materials can be made extensible by performing a mechanical operation, such as pleating, corrugating, or ring rolling the backsheet material. The backsheet 40 may be made extensible by forming it from a film made of a stretchable material such as Exxon film EXX-7 described above.

Typically, however, the films and the like used in constructing the backsheet 40 are unapertured, or if apertured, provided with open areas, or the like, are made liquid impervious by covering the open areas, closing the open areas, reducing the size of the open areas, or otherwise.

A particularly preferred extensible backsheet 40 is an extended adhesive film Formula #198-338 manufactured by the Findley Adhesives Company of Wauwatosa, Wis. The Findley adhesive film is a fluid impervious film capable of extending 200–300%. It is preferred because it is also elastically extensible.

This film can be used "as is" in the sanitary napkin 20. One side of the adhesive film can be adhered to the garment-facing side 42B of the absorbent core 42. The other side will comprise the garment-facing side 40B of the backsheet 40, and may be used as a panty fastening adhesive.

Alternatively, the side of the adhesive film that forms the garment-facing side 40B may have its adhesive surface at least partially covered (or "blocked" to eliminate its adhesive characteristics). The adhesive body-facing side 40A of the backsheet can also be at least partially blocked.

The exposed adhesive can be blocked in a number of suitable ways. These include, but are not limited to attaching a layer of nonadhesive material to cover the exposed adhesive, and brushing or sprinkling a powdered material such as talcum powder or corn starch on at least part of the exposed adhesive. The partial blocking of the exposed adhesive on the garment-facing side 40B of the backsheet 40 can be used with the remaining exposed adhesive to create particular panty fastening adhesive patterns.

In still other embodiments, an adhesive film can be created with one side that has adhesive tack, and one side without tack. One suitable adhesive film having these characteristics is a composite structure comprising a nonwoven elastomeric film with a low modulus pressure sensitive adhesive, such as adhesive film Formula #198-338 which is available with a blocking film such as film Formula H2301 from the Findley Adhesives Company. Such materials are further described (and used for other purposes) in U.S. Pat. No. 5,032,120 issued to Freeland, et al. on Jul. 16, 1991, and U.S. Pat. No. 5,037,416 issued to Allen, et al. on Aug. 6, 1991.

In other preferred embodiments, the backsheet 40 can comprise an extensible laminate structure. Such a laminate can be comprised of two or more layers. The laminate can be comprised of layers each of which are capable of different extensibility. For instance, a backsheet 40 could comprise a laminate formed of a layer of Findley adhesive film that is covered on one or both sides by an extensible nonwoven web or by an extensible film.

D. Combinations of Topsheet, Backsheet, and Core Materials.

The sanitary napkin 20 of the present invention can be comprised of many different combinations of the topsheet, backsheet, and core materials described herein.

As noted above, the sanitary napkin 20 may be comprised of all extensible components. The sanitary napkin 20 shown in FIGS. 1–3 could, for instance, comprise a topsheet, backsheet, and absorbent core selected from any of those materials described above. The different types of topsheet, backsheet, and absorbent core materials could be assembled in any of many possible combinations.

Alternatively, as noted above, the sanitary napkin 20 may be comprised of some extensible components and some inextensible components. The sanitary napkin could, for instance, be comprised of at least one of the extensible components described herein combined with any conventional inextensible materials, or with at least some of the basic materials described above prior to providing these materials with extensibility to form many different structures. This can be done to achieve some desirable performance characteristic, or to reduce the overall cost of the sanitary napkin 20.

Figure 23A:
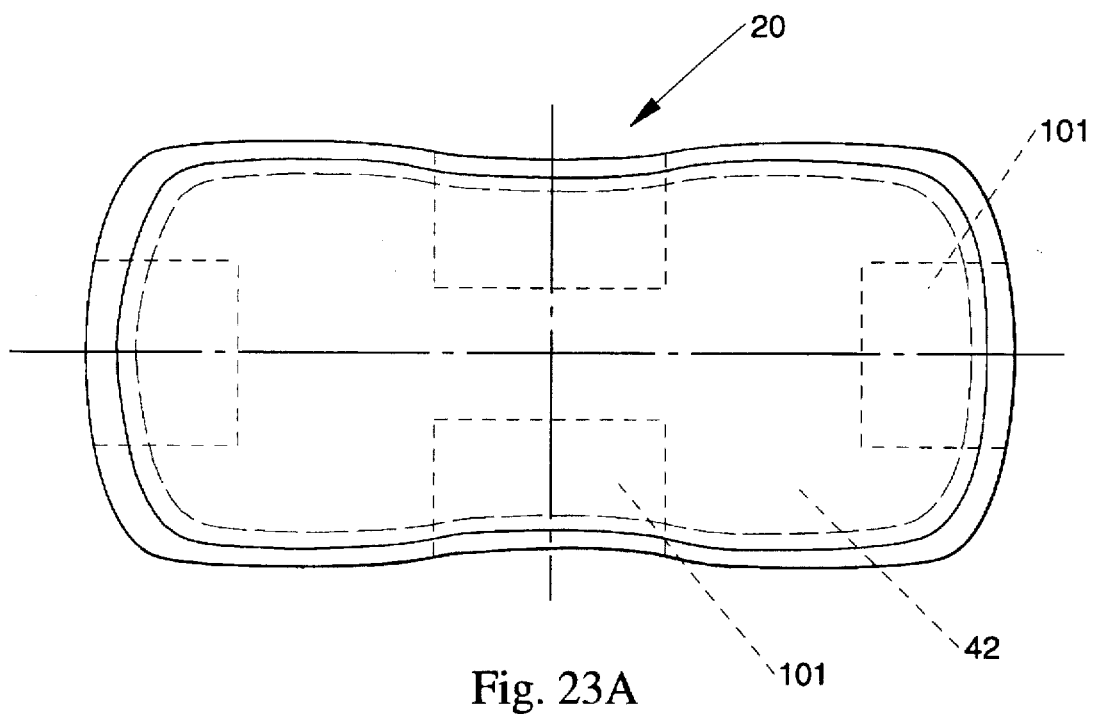
FIG. 23A is a schematic top plan view of a sanitary napkin formed with some extensible components and some inextensible components.
Figure 23B:
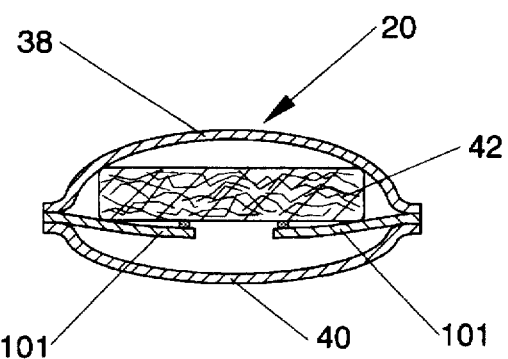
FIG. 23B is a schematic cross-sectional view of a sanitary napkin formed with some extensible components and some inextensible components.
Figure 23C:
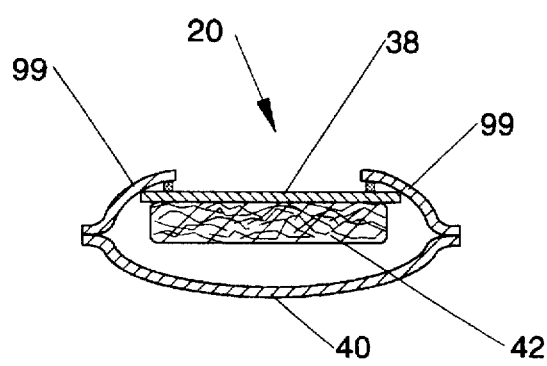
FIG. 23C is a schematic cross-sectional view of another sanitary napkin formed with some extensible components and some inextensible components.

FIGS. 23A–23C show some non-limiting examples of sanitary napkins formed with some extensible and some inextensible components. Many other examples exist, as well, and are within the scope of the present invention.

FIGS. 23A and 23B show a sanitary napkin 20 having an extensible topsheet 38 and backsheet 40 and an inextensible absorbent core 42. The absorbent core 42 is suspended relative to the topsheet 38 and backsheet 40 by extensible strips or bands of material 101. The extensible strips 101 are secured to the topsheet 38 and the backsheet 40.

The absorbent core 42 in such an embodiment, thus, forms a sling-like structure positioned between the topsheet 38 and backsheet 40, and the topsheet 38 and backsheet 40 form an extensible bag-like structure around the absorbent core 42.

The sanitary napkin 20 shown in FIGS. 23A and 23B (especially the backsheet 40 of the same) can, thus, extend with the wearer's panties for fit and comfort. The inextensibility of the core 42 is advantageous in that it allows the capillary characteristics of the absorbent core 42 to be maintained even when the topsheet 38 and backsheet 40 are extended.

FIG. 23C shows a sanitary napkin 20 having an extensible backsheet 40 that is combined with an inextensible topsheet 38 and an inextensible absorbent core 42. The sanitary napkin 20 shown in FIG. 23C provides a similar advantage to the sanitary napkin shown in the preceding figure. The sanitary napkin 20 in FIG. 23C, however, also provides several additional advantages.

The inextensibility of the topsheet 38 also allows the topsheet 38 to maintain its capillary characteristics (which often forms a composite absorbent system with the absorbent core 42) when the backsheet is extended.

The sanitary napkin 20 shown in FIG. 23C also allows the components that are intended to be near the wearer's body (the topsheet 38 and core 42) to fit adjacent the wearer's body without stretching. The backsheet 40 which needs to adjust to the stretching of the wearer's panties, can do so.

The sanitary napkin 20 shown in FIG. 23C also has a pair of longitudinally oriented extensible strips 99 along the body-facing side of the sanitary napkin. The strips 99 can comprise a nonwoven material, or some other suitable material. The strips 99 are preferably soft to provide a more comfortable surface for the wearer. The strips 99 also connect the topsheet 38 to the backsheet 40. The strips 99 may, thus, serve as "isolation elements" (described below) which permit the backsheet 40 to extend and stretch more independently of the topsheet 38 and absorbent core 42 than if such strips were not present.

Several other alternative sanitary napkin embodiments having some extensible components and some inextensible components are those which have stretch attachment means for fastening to the wearer's panties. These are described below in Section 4A(1).

In addition to combining various different topsheet, backsheet, and core materials, some of the materials specified herein can be used to serve more than one function, or as more than one component in an absorbent article.

For instance, some of the foam materials described herein as being suitable for use as an absorbent core can serve the functions of a topsheet, an absorbent core, and a backsheet. This can be accomplished by applying an impervious coating to the garment-facing side of the foam material, or otherwise treating the garment-facing side of the foam material to render it liquid impervious. In another embodiment, the topsheet 38 may be eliminated, and the underlying layer can serve the function that the topsheet 38 generally serves.

In addition, some of the materials described herein as being suitable for use as one component, such as a topsheet (or as a backsheet or core), can be used as one or more of the other components. (That is, provided that material has, or is modified to have, the desired characteristics for the component.)

Further, the manners described herein of making one of the components (such as the topsheet, backsheet, or core) extensible can generally be used to make any of the other components extensible.

E. Assembly of the Topsheet, Backsheet, and Absorbent Core.

The components of the sanitary napkin described above (the topsheet, backsheet, and absorbent core) can be secured together in any suitable manner that allows the sanitary napkin 20 to extend.

In the preferred embodiment shown in FIG. 1, the components of the sanitary napkin 20 are sized so that the edges of the topsheet 38 and backsheet 40 extend outward beyond the edges of the absorbent core 42. The backsheet 40 comprises a stretchable adhesive film. The core 42 is placed on top of the backsheet 40. The topsheet 38 is then placed on top of the core 42. The portions of the edges of the topsheet 38 that extend outward beyond those of the core 38 are secured to those of the backsheet 40.

As shown in FIG. 1, the topsheet 38 is also preferably secured to backsheet 40 along a first seam, such as seam 90. Seam 90 is preferably liquid impervious. The seam 90 can be formed by any means commonly used in the art for this purpose such as by gluing, crimping, or heat-sealing. The seam 90 is illustrated on the winged product shown in FIG. 5 as extending completely around the periphery of the main body portion 21.

It has been found that such a construction adequately secures the components of the sanitary napkin without securing the faces of the adjacent components to each other. Although, as noted above, it is often preferred to secure some of the components at their faces, as well.

The above is a preferred embodiment for ease of construction. (Other means of uniting the various components can be used.)

For instance, the present invention also includes so-called "tube" products. In these products, a liquid pervious cover material (such as topsheet material) can be wrapped completely around the absorbent core and the backsheet, and then the components can be secured together. In alternative arrangements, the topsheet could be wrapped around the core, and the wrapped core could be placed on and secured to the backsheet.

F. Fasteners for Attaching the Sanitary Napkin to the Wearer's Panties.

(1) General Characteristics of Preferred Fasteners.

The garment side 40B of the backsheet 40 may include fasteners (or "means for attaching the sanitary napkin to the undergarment of the wearer" or "attaching means")

FIG. 3 generally shows the central pad fastener, such as central pad adhesive 44 which is adapted to secure the sanitary napkin 20 to the crotch region of an undergarment. The central pad fastener 44 secures the main body portion 21 in the crotch portion of a panty.

FIG. 5 shows the flap fastener, such as flap adhesive 45. The flap adhesives 45 are used to assist in maintaining the flaps 52 in position after they are wrapped around the edges of the crotch portion of the panty as described below. The flap adhesive 45 is located on the outer surface of flap 52, adjacent the distal edges 53 of the flaps 52 {i.e., the end of the flaps 52 farthest away from the longitudinal centerline L of the sanitary napkin 20). The flaps 52 can be maintained in position by attaching the flaps 52 to the undergarment, or to the opposing flap.

The adhesive fasteners are respectively covered by removable cover strips or release liners, such as central pad release liner and flap release liner, both designated 50. The adhesives should be covered with release liners 50 to keep the adhesives from sticking to extraneous surfaces prior to use. Suitable release liners are described in U.S. Pat. No. 4,917,697.

The fasteners have been initially described in terms of adhesives for simplicity of description. The types of fasteners are not limited to adhesives, however. Preferred fasteners include but are not limited to adhesive fastening means, such as pressure sensitive adhesives, mechanical fasteners and combinations of adhesives and mechanical fasteners. The preferred types of fasteners and configurations thereof are described in greater detail below.

(a) Adhesive Fasteners.

Pressure sensitive adhesives, if used, may be applied to the garment side 40B of the backsheet 40 in many different patterns or configurations.

The adhesive configurations may be used for a variety of purposes in thin, flexible sanitary napkins. International Patent Application Publication No. WO 92/04000 entitled "Shape and Adhesive Fastening Means for an Absorbent Article" published in the names of Papa, et al. on Mar. 19, 1992, incorporated by reference herein, discloses configurations can be used to: (1) allow the sanitary napkin to conform to the body of the wearer; (2) reduce the tendency of the longitudinal edges of the sanitary napkin to roll over and bunch, and the tendency of the end edges to flip over and bring the panty adhesives in contact with the wearer's body and pubic hair.

The Papa, et al. patent application teaches that the overall width of the adhesive fasteners should be as close as possible to the width of the crotch region of the wearer's panties to reduce the tendency of the panty elastics to apply forces that flip back the longitudinal edges of the napkin. The Papa, et al. patent application also teaches that in at least some embodiments, there should be an area along the longitudinal centerline L of the sanitary napkin 20 where the backsheet 40 is unattached to the wearer's panties to allow this central portion of the backsheet 40 to separate from the panties and the sanitary napkin to deform into a W-shape in transverse cross-section similar to that shown in FIG. 69.

The Papa, et al. patent application teaches that the adhesive should be close to the end edges 24 of the sanitary napkin to reduce end flipping, but not too close. The adhesive should not be too close to the end edges 24 because the slightest amount of end flipping will cause the adhesive to come in contact with the wearer's body. The adhesive should preferably be no more than about 6 mm. from the end edges 24, and most preferably no more than about 6 mm. plus or minus about 3 mm.

The adhesive configurations in the present invention can be used to accomplish these same purposes, and to provide sanitary napkins that adjust to the dynamic changes of the wearer's body and panties when the sanitary napkin is worn.

The adhesive configurations that can be used depends on whether extensible or inextensible adhesives are used. The portion of the sanitary napkin on which extensible adhesives are located will be extensible. Sanitary napkins containing inextensible adhesives will typically only be capable of extension between the inextensible adhesive patches. Therefore, if inextensible adhesives are used, they are preferably applied in intermittent patterns to permit the sanitary napkin to extend between adhesive patches.

The adhesive can be applied in many configurations, including, but not limited to the following: (1) a single zone or patch of adhesive; (2) two parallel longitudinally-oriented strips on opposite sides of the longitudinal centerline; (3) two inwardly-arcuate strips of adhesive; and (4) multiple patches of adhesive. The adhesive can be applied in continuous or intermittent patterns in the above configurations (and other configurations) if the adhesive is extensible. As indicated above, if the adhesive is not extensible, it is preferably applied in intermittent patterns, including but not limited to intermittent dots, intermittent strips, and the like.

FIG. 3 shows one preferred adhesive configuration for use on the sanitary napkin of the present invention.

The adhesive configuration shown comprises six ¾"×¾" (about 2 cm.×2 cm.) square pieces and two ¾"×2.5" (about 2 cm.×6.4 cm.) longitudinally-oriented rectangular pieces. One rectangular piece is positioned on each side of the longitudinal centerline L. The square pieces are placed in the end regions 28 and 30 of the sanitary napkin. The square pieces are placed so that in each end region, one piece is in each corner 27, and one is disposed along the longitudinal centerline.

The adhesive patches 44 can each be covered with a separate cover strip 50. However, the patches are preferably covered with a single release sheet. This allows for ease of manufacture and benefits the consumer who does not have to dispose of several small individual cover strips 50.

If the adhesives are extensible, they preferably extend approximately the same amounts as the sanitary napkin as set forth in Table 1.

Suitable extensible adhesives include extensible adhesives, per se, and extensible adhesive/backsheet combinations. Any extensible adhesives known in the art can be used. Suitable extensible adhesive/backsheet combinations include, but are not limited to non-extensible adhesive used on an extensible backsheet material known as 3 Sigma 2474 available from Anchor Continental, Inc., 3 Sigma Division, of Covington, Ohio; elastically stretchable adhesive films such as Findley adhesive 198–338, or an elastically stretchable adhesive film known as 3M XPO-0-014 available from the Minnesota Mining and Manufacturing Company of St. Paul, Minnesota; or spray adhesives such as 3M adhesive 1442 on a low modulus elastic film.

Suitable inextensible adhesives may be those adhesives specified as 0.6 mil pass available from Century Adhesive as product number A305-4, or from Anchor Continental, Inc., 3 Sigma Division, of Covington, Ohio. Suitable inextensible adhesive fasteners are described in greater detail in U.S. Pat. No. 4,917,697.

(b) Mechanical Fasteners, Frictional Fasteners, and the Like.

The fasteners used with all of the various embodiments of the present invention described herein are not limited to adhesive attachment means. Any type of fastener used in the art can be used for such purpose.

For example, the sanitary napkin 20 could be secured to the wearer's undergarment by conventional VELCRO hook material, or by the fasteners described in U.S. Pat. No. 4,946,527 issued to Battrell on Aug. 7, 1990, U.S. Pat. No. 5,058,247 and 5,116,563 issued to Thomas, et al. on Oct. 22, 1991 and May 26, 1992, respectively, and EPO patent application publication No. 0 381 087 published Aug. 8, 1990, or high coefficient of friction foams and other high coefficient of friction materials such as those described in U.S. Pat. No. 4,166,464 issued to Korpman, U.S. Pat. No. 4,834,739 issued to Linker, III, et al., and U.S. Pat. No. 5,011,480 issued to Gossens, et al.

The stretching forces exerted on the garment surface 20B of the sanitary napkin 20 by the wearer's panties, moving in response to the wearer's body motions accounts for many of the problems that lead to adhesive fasteners becoming unattached from the wearer's panties. The use of mechanical fasteners on stretchable absorbent articles is believed to be particularly beneficial, due to their tendency to reduce the effect of these shearing forces. Mechanical fasteners that engage the fabric of the wearer's panties will move with the panties, reducing the problems caused by these shearing forces.

G. Optional Components of the Sanitary Napkin

The sanitary napkin 20 of the present invention may be provided with optional additional components. (If desired, these additional components may be provided with extensibility in any of the manners described herein.)

Figure 6:
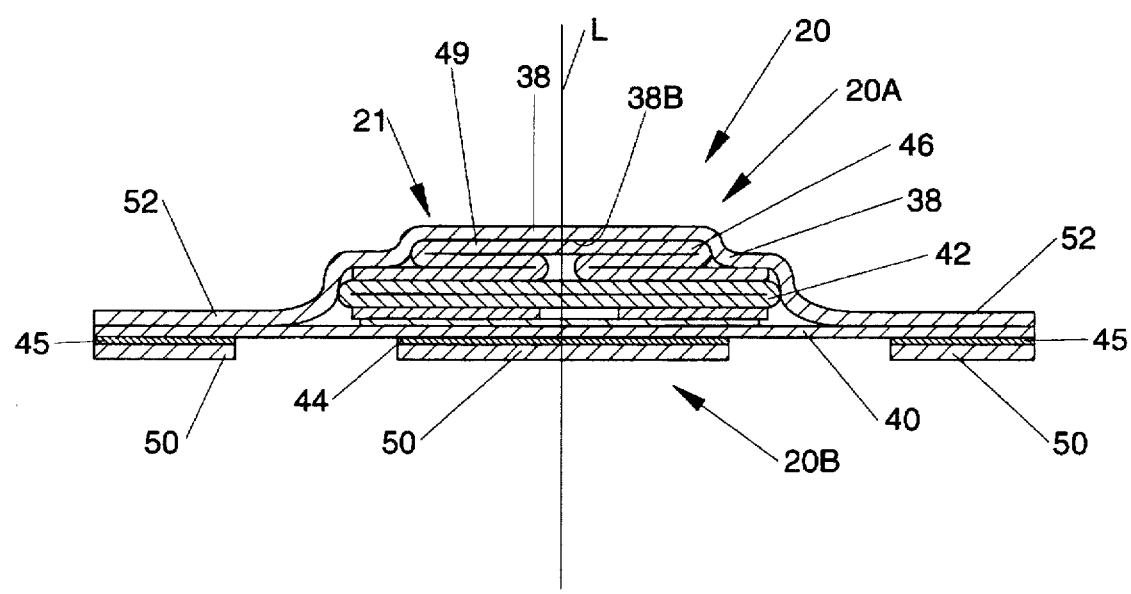
FIG. 6 is a simplified transverse cross-sectional view taken along line 6—6 of FIG. 5.

The sanitary napkin 20 of the present invention can be provided with one or more additional pervious or absorbent layers. The additional pervious or absorbent layers may be positioned between the absorbent core 42 and either the topsheet 38, the backsheet 40, or both. As shown in FIG. 6, an absorbent layer, such as wicking layer 46, is positioned between the topsheet 38 and the absorbent core 42. This wicking layer 46 may be referred to as a secondary topsheet, or "wipe acquisition sheet", or "acquisition layer".

In the embodiment shown in FIG. 6, the acquisition layer 46 is a folded sheet of nonwoven material. It should be understood, however, that the acquisition layer 46 need not be a folded sheet. The terms "layer" or "web", as used herein to describe the acquisition layer, include, but are not limited to single unfolded sheets, folded sheets, strips of material, loose or bonded fibers, multiple layers or laminates of material, or other combinations of such materials. The terms layers and webs are thus, not limited to single unfolded layers or sheets of material.

In FIG. 6, the acquisition layer 46 is a "double" z-folded sheet. The sheet 46, is more specifically folded so that when the sanitary napkin is cut along the transverse centerline T, the left half of the folded sheet appears as a reverse "z" in cross section and the right half appears as a "z". The sheet 46 is preferably folded so that it has an upper portion 49 that appears as a rectangular strip in plan view. The upper portion 49 of the acquisition layer 46 is preferably about 227 mm long, and between about 25 and about 38 mm wide. The upper portion 49 preferably has a caliper of from about 0.5 mm up to about 4 mm (the higher end of this range creates thicker products). Such a folded arrangement is described in greater detail in PCT Patent Application Publication No. WO 92/07535 published in the name of Visscher, et al. on May 14, 1992.

FIG. 7 is a simplified cross-sectional view similar to that of FIG. 6, showing an alternative arrangement of the components of the sanitary napkin 20. In FIG. 7, rather than being a separate layer that is located on top of the core 42, the acquisition layer 46 is an integral layer (or component) that comprises the top layer of a laminated absorbent core 42 structure.

The acquisition layer 46 serves to improve wicking of exudates over and into the absorbent core 42. There are several reasons why the improved wicking of exudates is important. The improved wicking provides a more even distribution of the exudates throughout the absorbent core.

The improved wicking also allows the sanitary napkin 20 of the present invention to be made relatively thin. The acquisition layer 46 is capable of dispersing exudates over a large surface area of the absorbent core 42. The acquisition layer 46 thus allows the sanitary napkin 20 to absorb relatively large amounts of exudates. Bulky prior art sanitary napkins relied on a high degree of vertical absorption at the point where exudates are initially deposited. Because the absorbent cores of these prior napkins were fairly thick, they could absorb a large volume of exudates while utilizing only a small degree of the surface area or lateral absorption capacity. The thin versions of the sanitary napkins 20 of the present invention may absorb relatively large amounts of exudates because the wicking disperses the exudates over a large surface area of the absorbent core 42 where the exudates can better and faster be vertically absorbed into the absorbent core 42.

The acquisition layer 46 may also be used to direct exudates toward the ends of the core 42D. Liquid exudates that are deposited on the core 42 will tend to be distributed radially outward from the place where they are deposited. Since the core 42 of the sanitary napkin 20 is relatively narrow in comparison to its length, liquid exudates will reach the longitudinal edges 42C of the core 42C much sooner than they will reach the ends 42D of the absorbent core. The acquisition layer 46 can be used to longitudinally wick and direct exudates toward the ends 42D of the core 42. This more effectively utilizes the capacity of the core, and reduces the possibility of leakage caused by exudates prematurely reaching the longitudinal edges 42C of the core.

The characteristics of the acquisition layer 46 are as follows. The acquisition layer 46 should be liquid permeable. The acquisition layer 46 is also preferably compliant, soft feeling, and non-irritating to the user's skin. It can be made from any materials that are capable of dispersing exudates in the preferred manner described above. The materials may also be capable of having the topsheet 38 fused to them. The acquisition layer 46 is preferably provided with stretch properties. The acquisition layer 46 has a body-facing face (or side) 46A, and a garment-facing face 46B.

The acquisition layer 46 should be hydrophilic. The fibers or yarns 55 comprising the acquisition layer 46 may be inherently hydrophilic. Alternatively, they may be treated to render them hydrophilic. Suitable methods for rendering fibers hydrophilic include treating them with a surfactant. The fibers can be treated by spraying the material comprising the acquisition layer with a surfactant or immersing the material into the surfactant. A more detailed discussion of such a treatment and hydrophilicity is contained in U.S. Pat. No. 4,988,344 and 4,988,345 issued to Reising, et al. and to Reising, respectively. The hydrophilicity of these fibers allows the acquisition layer 46 to draw liquid exudates through the topsheet 38 from below.

The acquisition layer 46 may be comprised of many of the same materials as the absorbent core. The acquisition layer 46 may be comprised of woven or nonwoven materials. These materials may be synthetic, or partially synthetic and partially natural materials. Suitable synthetic fibers include polyester, polypropylene, polyethylene, nylon, viscous rayon fibers, or cellulose acetate, with polyester fibers being preferred. Suitable natural fibers include cotton, cellulose, or other natural fibers. The acquisition layer 46 may also be at least partially comprised of cross-linked cellulose fibers, or as in the case of the preferred embodiments described in the Examples set forth below, capillary channel fibers.

The acquisition layer 46 can also be comprised of combinations of the above materials, such as blends of fibers similar to those described above for use in the blended absorbent core, or any equivalent material or combinations of materials.

The fibers or yarns 55 comprising the acquisition layer 46 may be of any length, from staple length to continuous filaments. The length of the fibers 55 is preferably between about 1 inch and about 3 inches (between about 2.5 cm. and about 7.5 cm.), and most preferably is about 1.5 inches (about 3.8 cm.). The fibers 55 preferably have a denier per filament of between about 1 and about 3, most preferably about 1.5.

The fibers 55 of the acquisition layer 46 are preferably oriented primarily in a single direction. Typically, the acquisition layer 46 can be manufactured with its fibers oriented in the machine direction (MD). The acquisition layer 46 can be placed in the product with most of the fibers 55 oriented in either the longitudinal direction or the transverse direction. (That is, the fibers 55 are generally parallel to either the longitudinal or transverse centerlines L of the sanitary napkin 20).

The phrases "generally parallel" to one of the centerlines, as used herein, are intended to include fibers that angle away from the respective centerline. The fibers are considered to be generally parallel to the longitudinal centerline as long as they are oriented more in the longitudinal direction than the transverse direction.

The orientation of the fibers 55 in the acquisition layer 46 in the longitudinal direction may be used to cause liquid exudates deposited on the acquisition layer 46 to preferentially wick and be distributed toward the ends 42D of the absorbent core 42. If the fibers 55 in the acquisition layer are generally parallel to the longitudinal centerline L, however, some operation, such as ring rolling, generally must be performed on the acquisition layer 46 for the acquisition layer to be extensible in the longitudinal direction.

The acquisition layer 46 may be any suitable size. The acquisition layer 46 need not extend the full width of the absorbent core 42. The acquisition layer 46 could, for instance, be in the form of a strip positioned similarly to (and of a size similar to) the upper portion 49 of the z-folded sheet shown in FIGS. 5 and 6.

The acquisition layer 46, if nonwoven, can be made by a number of different processes. These include, but are not limited to the following in order of preference from least to most preferred: meltblown, spunbonded, carded, the latter including, in order of preference, thermally-bonded, air-through bonded, powder bonded, latex bonded, solvent bonded, or most preferably, spunlaced. The latter processes are more preferred because it is easier to orient the fibers in a single direction in such processes.

Suitable commercially available products for use as the acquisition layer 46 include a 70%/30% rayon/polyester fabric known as SONTARA. The SONTARA fabric is described in greater detail in U.S. Pat. NOS. 4,950,264 and 5,009,653 issued to Osborn.

In a particularly preferred embodiment, the acquisition layer 46 comprises a spunlace nonwoven web comprised of permanently wettable fibers. Preferably, the acquisition layer 46 is a 30 g/yard$^2$ (35 g/m$^2$) polyethylene terephthalate (or PET) spunlace nonwoven web. Spunlaced fabrics of this type are manufactured by the Veratec Company of Walpole, Mass. The spunlace nonwoven web is formed in such a way that most of the fibers are oriented in a single direction.

The fibers of this particularly preferred acquisition layer 46 material are made of a PET resin and are coated with the permanently wettable CELWET finish. The term "permanently wettable", as used herein, refers to fibers that will sink in less than or equal to about 7 seconds when tested according to the ASTM D 1117-74 Basket Sink Method.

The CELWET finish is particularly preferred for use in sanitary napkins having a topsheet 38 comprising an apertured film or scrim with hydro-entangled nonwoven fibers such as that described in U.S. patent application Ser. No. 07/810,744 filed in the name of Cree, et al. on Dec. 17, 1991, because fibers coated with it remain extremely hydrophilic after hydro-entangling processes, and therefore, wick blood very well.

In another particularly preferred embodiment, the acquisition layer 46 comprises a spunbonded polypropylene nonwoven CELESTRA fabric known as P-9 manufactured by the Fiberweb Group.

If desired, the sanitary napkin 20 may be additionally provided with flaps 52 that extend outwardly from each longitudinal edge 22 of the sanitary napkin 20. The flaps 52 may be in any suitable configuration. Suitable flaps 52 may, for example, be made in accordance with the teachings of U.S. Pat. No. 4,589,876, issued May 20, 1986 to Van Tilburg and 4,687,478, issued Aug. 18, 1987 to Van Tilburg, U.S. patent application Ser. No. 07/769,891 entitled "Absorbent Article Having Flaps and Zones of Differential Extensibility" filed Oct. 1, 1991 in the name of Lavash, et al., U.S. patent application Ser. No. 07/832,246 entitled "Absorbent Article Having Inwardly-Folded Pleated Flaps filed Feb. 7, 1992 in the name of Niihara, et al., Ser. No. 07/707,233 entitled "Sanitary Napkin Having Laterally Extensible Means for Attachment to the Undergarment of the Wearer", filed May 21, 1991 in the name of Osborn, et al.,the disclosures of which patents are incorporated herein by reference.

The following Examples further illustrate the practice of the present invention, particularly those sanitary napkins which utilize capillary channel fibers in the construction of the same. The following Examples, however, are not intended to limit the scope of the absorbent articles encompassed therein.

EXAMPLE I

Thick Pad

A sanitary napkin article is hand-made using the following components. Reference is made to FIG. 18 for the assembly of the product.

The topsheet 38 is made in accordance with U.S. Pat. No. 4,463,045 and ring rolled to provide it with longitudinal extensibility.

The absorbent core 42 is a superabsorbent material laminate as described above which is slitted or partially slitted for longitudinal extensibility. FIG. 18 shows an absorbent core 42 that is slit at the end regions 28 and 30, but not at the central region 32. The backsheet 40 is an extended adhesive film known as Formula #198-388 manufactured by the Findley Adhesives Company of Wauwatosa, Wis.

The sanitary napkin 20 shown in FIG. 18 also preferably comprises a layer of capillary channel fibers 150. The thick pad comprises a swatch 152 of capillary channel fibers. In the thin sanitary napkin described in Examples II and III below, the swatch 152 of fibers is eliminated, and the layer of capillary channel fibers may be gathered at the center into a tuft 154. The sanitary napkin 20 further comprises a creped BOUNTY (TM) paper towel layer 156 and polyethylene end guards 158.

FIG. 18 shows one preferred adhesive configuration for use on this extensible sanitary napkin embodiment. The adhesive configuration shown comprises six ¾"×¾" (about 2 cm.×2 cm.) square pieces of adhesive 44 and two ¾"×2.5" (about 2 cm.×6.4 cm.) longitudinally-oriented rectangular pieces 44. One rectangular piece is positioned on each side of the longitudinal centerline L. The square pieces are placed in the end regions 28 and 30 of the sanitary napkin 20. The square pieces are placed so that in each end region, one piece is in each corner 27, and one is disposed along the longitudinal centerline L.

The adhesive patches 44 can be extensible, inextensible, or some patches can be extensible and some inextensible.

The adhesive patches 44 can each be covered with a separate release liner or cover strip 50. However, the patches are preferably covered with a single release sheet for ease of manufacture and so that the consumer does not have to dispose of several small individual cover strips 50. Any commercially available release liner can be used. In one preferred embodiment, the release liner could be replaced by a wrapper that provides both an individually packaged sanitary napkin and a container for disposing the sanitary napkin after use, such as is described in U.S. Pat. No. 4,556,146 issued to Swanson, et al. on Dec. 3, 1985.

The capillary channel fibers are preferably substantially curled. Suitable capillary channel fibers are those designated SW194 available from the Eastman Chemical Company. The SW194 fibers comprise a carded staple sliver which has been stuffer box crimped to 7.8 crimps per inch and have an H-shaped cross-section with a channel width of 37 microns, a channel depth of 48 microns, and a denier of approximately 22 dpf. The capillary channel fibers are preferably 6 in. long; 0.75 g. fibers are used.

In the making procedure, the ring rolled topsheet is cut to the desired size, a template (2"×7" opening) is placed on the back side of the topsheet and sprayed with the Findley 4031 adhesive. The adhesive is applied in a spiral pattern (see FIG. 1BA).

The layer of capillary channel fibers SW194 is hand-pressed in the center of the glue sprayed area with the fibers running parallel to the long axis of the topsheet. The capillary channel fibers are preferably pressed into the center of the glued area so that they at least partially cover at least some apertures of the topsheet. The capillary channel fibers may also at least partially protrude into the apertures of the topsheet.

The capillary channel fibers SW173 are hand pressed as a swatch (with fibers parallel to the long axis of the article) in the center of the layer capillary channel SW194 fibers. This provides a Pre-Assembly of the topsheet and capillary channel fibers.

For convenience, the remainder of the procedure is carried out using a concave forming die. The Findley adhesive backsheet (polyethylene backsheet with adhesive coating and release paper) is placed in the form. The slitted superabsorbent (or absorbent gelling material, or "AGM") laminated core is placed over the backsheet, and the creped tissue (BOUNTY) is placed over the AGM core. The Pre-Assembly, prepared above, is placed over the creped tissue. With the Pre-Assembly over the creped tissue, the article's components are pulled snugly over the edges of the form, but not so tightly that the components begin to pull away from the form. Firm pressure is applied to adhere the edges with the adhesive on the backsheet.

The article is removed from the form and the ends are pressed in place using a roller. The release paper is peeled from the back of the backsheet. The end guard polyethylene strips are added and the strips of panty fastening adhesive are placed on the article. The outer surface of the topsheet is sprayed with 0.01 g of PEGOSPERSE surfactant available from Lonza, Inc., Williamsport, Pa. The specifications of the finished product are as follows.

| Parameter | Specifications |
| --- | --- |
| Pad weight (g) | 9.82 ± 0.12 |
| Core weight (g) laminate only | 2.57 ± 0.04 |
| Pad length (mm) | 226 ± 1 |
| Core length (mm) | 197 ± 1 |
| Pad width at center (mm) | 81 ± 2 |
| Core width at center (mm) | 70 ± 0 |
| Pad caliper (inches at 0.13 psi) | 0.611 ± 0.02 |
| Core caliper (inches at 0.13 psi) | 0.058 ± 0.003 |
| Seal length (mm) | 8 ± 1 |
| Components | |
| Polyethylene ring rolled formed-film topsheet (according to U.S. PAT. 4,463,045) | ca. 9" × 5" |
| Capillary channel fibers SW194 (Eastman) | 1.5 g |
| Capillary channel fibers SW173 (Eastman) | 0.5 g. |
| Findley extensible adhesive film backsheet (Formula #198-338) | 9" × 5" |
| Creped BOUNTY paper towel | Shaped* |
| Panty fastening adhesive | Six ¾" × ¾" pieces; two ¾" × 2.5" pieces |
| Release paper | As needed |
| Surfactant (PEGOSPERSE) | 0.01 g |
| White poly for ends | 4" × 0.75" |
| Absorbent gelling material (AGM) slit core non-slit central area; total core wt. 2.6 g; contains 0.7 g polyacrylate AGM | 70 mm × 193 mm with 2-¾" non-slit center area |
| Findley Adhesive-4031 | 0.05 g |

*See FIG. 18(38) for shape. The shape is designed to provide anatomical fit.

EXAMPLE II

Thin Pad

Reference is made to FIG. 18. The assembly of the thin pad is equivalent, except that CCF SW173 fibers are used in place of the layer of CCF SW194 fibers (150), and no swatch (152) of fibers is used.

Assembly of the product is as follows. Cut capillary channel fibers (CCF SW173) to 7 in. length; 0.75 g fibers used. Cut the ring-rolled topsheet to size. Place the template on the bottom side of the topsheet and apply Findley 4031 adhesive (spiral pattern). Hand-press CCF SW173 fibers in the center of the glued area with the fibers running substantially parallel to the long axis of the topsheet. Lay the Findley backsheet on flat surface. Place the slitted AGM laminate core on the Findley backsheet. Center the creped BOUNTY tissue (shaped similarly to the topsheet) over the laminate core. Center the topsheet/capillary channel fiber Pre-Assembly over the creped tissue. Secure the Pre-Assembly and smooth at edges. Roll the edges to seal. Peel the release paper from the back of the pad. Tear and remove in 2 or 3 pieces, then place the poly on the ends of the article. Place the panty fastening device (PFA) on the pad. Spray the topsheet with 0.01 g. PEGOSPERSE surfactant. The specifications of the finished product are as follows.

| Parameter | Specifications |
| --- | --- |
| Pad weight (g) | 8.50 ± 0.18 |
| Core weight (g) laminate | 2.54 ± 0.09 |
| Pad length (mm) | 232 ± 4 |
| Core length (mm) laminate | 201 ± 1 |
| Pad width at center (mm) | 85 ± 1 |
| Core width at center (mm) | 65 ± 1 |
| Pad caliper (in. at 0.13 psi) | 0.211 ± 0.005 |
| Core caliper (in. at 0.13 psi) | 0.074 ± 0.003 |
| Components | |
| Polyethylene formed-film topsheet (ring rolled; per U.S. PAT. 4,463,045) | 9" × 5" |
| Capillary channel fibers SW173 (Eastman) | 0.75 g; 7" length |
| Findley extensible adhesive film backsheet (Formula #198-338) | ~9" × 5" |
| Creped BOUNTY paper towel | Shaped* |
| PFA (panty fastening adhesive) | Six ¾" × ¾" pieces and two ¾" × 2.5" pieces |
| Release paper | As needed |
| PEGOSPERSE | 0.01 g |
| White poly for ends | 4" × ¾" |
| AGM slit core non-slit center; total core weight 2.5 g; contains 0.7 g AGM | 65 mm × 193 mm with 2 ¾" non-slit center |
| Findley 4031 (adhesive) | 0.05 g |

*As in Example I.

As noted above, in one preferred mode of this stretchable sanitary napkin 20, the central portion of the layer 150 of capillary channel fibers can be gathered into a small "loop" or "tuft" 154. This loop or tuft 154 thus extends upward from the layer of capillary channel fibers to firmly contact the topsheet 38. Moreover, the loop or tuft 154 is positioned centrally in the overall article, such that it can provide rapid acquisition and transport of fluid into the remaining portion of the layer of capillary channel fibers, and thence into the fluid storage layer of the article.

Advantageously, such "loop" or "tuft" not only concentrates capillary channel fibers at the point where fluid impinges onto the article, but also orients the capillary channel fibers which comprise the loop or tuft substantially in the upward z-direction, thus enhancing fluid movement in the downward z-direction of the article. The following Example illustrates an absorbent article having a substantially central, z-directional tuft of capillary channel fibers.

EXAMPLE III

Pad With Central Tuft of Fibers

A layer of capillary channel fibers of the type disclosed herein (with a 6-inch length) is gathered in its center to provide a slightly raised oval "tuft" having the approximate dimensions: 2–3 inches x-direction (or longitudinal dimension); 1.5 inches y-direction (or lateral dimension) at widest point; and 5 mm–10 mm z-direction.

The tufted bundle of fibers can be held in its tufted configuration by any convenient means. Typically, the tuft is passed through a confining slit in a sheet of paper or hydrophilic polymer. Using the procedures disclosed herein, the tufted bundle of fibers is assembled into an absorbent article with the tuft residing approximately at the center of the overlying topsheet, and with the tuft in close contact with the topsheet, as explained hereinabove.

In use as a sanitary napkin, the article is positioned (e.g., intralabially) to maximize fluid uptake by the tuft. In an alternate mode, the ends of the looped fibers in the tuft are cut to provide a fleece-like, z-directional bundle of open-ended capillary channel fibers. In still another embodiment, the layer of capillary channel fibers comprising the base of the tuft is positioned wholly or partly within the wet-laid or dry-laid absorbent core of the article, rather than atop the core. In this latter embodiment, a commercially-available layered laminate core comprising two outer tissue layers with an intermediate layer of absorbent gelling material (AGM) can be used. The capillary channels at the base of the tuft can be slipped into the internal, AGM-containing layer.

EXAMPLE IV

Ultra-Thin Pad

Reference is made to FIG. 18. The assembly of the ultra-thin pad is equivalent, except that no swatches of capillary channel fibers are used.

Assembly of the product is as follows. Cut the ring-rolled topsheet to size. Place the template on the bottom side of the topsheet and apply Findley 4031 adhesive (spiral pattern). Lay the Findley backsheet on flat surface. Place the slitted AGM laminate core on the Findley backsheet. Center the creped BOUNTY tissue (shaped similarly to the topsheet) over the laminate core. Place the topsheet over the creped tissue. Secure the components and smooth at edges. Roll the edges to seal. Peel the release paper from the back of the pad. Tear and remove in 2 or 3 pieces, then place the poly on the ends of the article. Place the panty fastening device (PFA) on the pad. Spray the topsheet with 0.01 g. PEGOSPERSE surfactant. The specifications of the finished product are as follows.

| Parameter | Specifications |
| --- | --- |
| Pad weight (g) | 8.50 ± 0.18 |
| Core weight (g) laminate | 2.54 ± 0.09 |
| Pad length (mm) | 232 ± 4 |
| Core length (mm) laminate | 201 ± 1 |
| Pad width at center (mm) | 85 ± 1 |
| Core width at center (mm) | 65 ± 1 |
| Pad caliper (in. at 0.13 psi) | 0.11 ± 0.01 (2.9 mm) |
| Core caliper (in. at 0.13 psi) | 0.074 ± 0.003 |
| Components | |
| Polyethylene formed-film topsheet (ring rolled; per U.S. PAT. 4,463,045) | 9" × 5" |
| Findley extensible adhesive film backsheet (Formula #198-338) | ~9" × 5" |
| Creped BOUNTY paper towel | Shaped* |
| PFA (panty fastening adhesive) | Six ¾" × ¾" pieces and two ¾" × 2.5" pieces |
| | As needed |
| PEGOSPERSE | 0.01 g |
| White poly for ends | 4" × ¾" |

| Parameter | Specifications |
|---|---|
| AGM slit core non-slit center; total core weight 2.5 g; contains 0.7 g AGM | 65 m × 193 mm with 2 ¾" non-slit center |
| Findley 4031 (adhesive) | 0.05 g |

*As in Example I.

4. Alternative Embodiments.

In alternative embodiments, components of regions of the sanitary napkin may be structurally modified by folding, bending, corrugating, stacking of layers and affixing layers to each other. The modifications may be made by including one or more of the structures described in the aforementioned European patent applications published in the name of Buell, in the aforementioned U.S. patent application filed in the name of Visscher, et al., and in U.S. patent application Ser. No. 07/874,872 entitled "Generally Thin, Flexible Sanitary Napkin filed in the name of Osborn on Apr. 28, 1992.

In still other alternative embodiments, the sanitary napkin could be provided with additional components. For instance, the sanitary napkin could be provided with the wet-laid tissue and/or the liquid permeable wipe acquisition sheet described in greater detail in U.S. Pat. No. 5,009,653 issued to Osborn.

In yet other alternative embodiments, the sanitary napkin could be provided in a curved, shaped configuration such as that described in the following patent applications filed on the same date as the present application: U.S. patent application Ser. No. 07/915,285, entitled "Curved, Shaped Absorbent Article" filed in the name of Theresa L. Johnson, et al.; U.S. patent application Ser. No. 07/915,202, entitled "Absorbent Article Having Resilient Center" filed in the name of Thomas W. Osborn, et al.; U.S. patent application Ser. No., 07/915,201, entitled "Absorbent Article Fastener Pattern" filed in the name of Robb E. Olsen, et al.; and, U.S. patent application Ser. No., 07/915,134, entitled "Method of Making Curved, Shaped Absorbent Article" filed in the name of Letha M. Hines, et al.

Thus, while the sanitary napkins of the present invention may typically be comprised of components that extend together to a sufficient degree when stretched such that the extended configuration of the sanitary napkin is not curved, in other embodiments the extension of the components could result in a curved product.

While several preferred sanitary napkin embodiments have been described, numerous other sanitary napkin embodiments are disclosed in the literature. These could be provided with the stretch properties of the present invention. Some of such sanitary napkins are described in U.S. patent application Ser. No. 07/605,583 filed Oct. 29, 1990 in the name of Visscher, et al., U.S. Pat. Nos. 5,009,653 and 4,950,264, issued to Osborn on Apr. 23, 1991 and Aug. 21, 1990, respectively, U.S. Pat. No. 4,940,462, issued to Salerno on Jul. 10, 1990, U.S. Pat. No. 4,917,697 issued to Osborn, III, et al. on Apr. 17, 1990, U.S. Pat. No. 4,911,701 issued to Mavinkurve on Mar. 27, 1990, U.S. Pat. No. 4,900,320, issued to McCoy on Feb. 13, 1990, U.S. Pat. No. 4,687,478 issued to Van Tilburg on Aug. 18, 1987, U.S. Pat. No. 4,608,047 issued to Mattingly on Aug. 26, 1986, U.S. Pat. No. 4,589,876 issued to Van Tilburg on May 20, 1986, U.S. Pat. No. 4,285,343 issued to McNair on Aug. 25, 1981, U.S. Pat. No. 3,397,697 issued to Rickard on Aug. 20, 1968, and U.S. Pat. No. 2,787,241 issued to Clark on Apr. 2, 1957.

The terms "panty liner" or "pantiliner" refer to absorbent articles that are less bulky than sanitary napkins which are generally worn by women between their menstrual periods. Suitable absorbent articles in the form of pantiliners are disclosed in U.S. Pat. No. 4,738,676 entitled "Pantiliner" issued to Osborn on Apr. 19, 1988.

The term "incontinent article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the extensible components described herein are disclosed in U.S. Pat. No. 4,253,461 issued to Strickland, et al. on March 3, 1981; U.S. Pat. No. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991.

The focus of the present invention is on absorbent articles that are intended to be worn in the crotch region of the wearer's undergarments. However, the features of the present invention could also be used in absorbent articles such as diapers. Diapers are absorbent articles worn by infants and incontinent persons that are fastened about the waist of the wearer.

Suitable diapers that can be provided with the extensible features described herein are disclosed in U.S. Pat. No. 3,860,003 issued to Buell on Jan. 14, 1975, and U.S. patent application Ser. No. 07/715,152 filed in the name of Buell, et al. on Jun. 13, 1991.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

5. Test Methods The extensibility of the sanitary napkin (or other absorbent article) is measured on EME Tensile Tester, Model No. 559A available from EME, Inc., P.O. Box 187, Newbury, Ohio 44065, a constant rate of elongation tensile testing apparatus.

The EME Tensile Tester is provided with a computer that provides an LCD readout of the distance the ends of the clamps are spaced from a reference home position and the forces on the sample when the clamps are spaced various distances from the home position.

All tests are performed at 50% humidity and at 73° F. The samples are carefully handled to avoid any stretching of the same prior to performing the test. The tests should each be repeated with samples taken from five separate products of the same type. If any of the samples fall within the claimed range or limit, the product will be considered to fall within the scope of the appended claims.

A. Method to Measure Extensibility of One Inch (2.5 cm.) Center Strip.

STEP 1

Sample for Measuring Longitudinal Extensibility

Cut a 1.0 inch (2.54 cm.) wide strip from the center of the absorbent article using a JDC Precision Sample Cutter, Model #1-12 available from Thwing-Albert, Philadelphia, Pa. The strip used as the sample for this method should be cut along the longitudinal centerline of the absorbent article. The length of the strip should run the full length of the portion of the absorbent article from which the sample is taken.

Sample for Measuring Transverse Extensibility

A 1.0 inch wide strip is cut from parallel to the transverse centerline of the absorbent article using the JDC sample cutter. The strip used as the sample for measuring the transverse extensibility can be cut through any one inch wide section of the absorbent article that runs parallel to the transverse centerline. The sample need not run along the transverse centerline.

The sample should, however, be cut through a portion of the absorbent article so that the entire one inch width of the sample consists of at least one of the absorbent components of the absorbent article. (The term "absorbent component" is defined below.) Thus, the sample should not be cut so close to one of the transverse end edges of the absorbent article that the sample contains portions of the absorbent article at the end seal.

Samples for Measuring Both Longitudinal and Transverse Extensibility

A sample for measuring longitudinal extensibility should be cut from a first sample absorbent article. The sample for measuring transverse extensibility should be cut from a second sample absorbent article of the same type as the first (i.e., an identical product). (The same applies to any of the other tests described herein when a sample is cut out of the product to measure extensibility in a given direction.)

STEP 2

Remove any adhesive cover strip from the sample. If the sample has an adhesive fastener, eliminate any adhesive tack by dusting the adhesive fastener with talc or corn starch.

STEP 3

Lay the sample unrestrained on a table with the body surface facing upward. Measure the length of the sample to the nearest 0.1 inch (0.25 cm.).

The length of the sample, for the purpose of the appended claims, is the dimension of the sample that runs perpendicular to the one inch width dimension. The length of the sample is obtained by measuring the length of the absorbent components of the sample. (This can be contrasted with determining the length of the sample by simply measuring the overall length of the sample.)

The length of the sample is equal to the length of the longest absorbent component of the sample. If the sample is folded or curved (i.e., when it is removed from its package), flatten the ends of the sample prior to measuring the length of this absorbent component. The sample is flattened by placing a ruler on top of the sample and gently pressing down on the portion of the ruler that covers the ends of the sample until the garment surface at the ends lies flat against the table.

The term "absorbent component", as used herein, refers to components that are generally used as the primary absorbent component of the product, such as the absorbent core of the product. It also includes absorbent components, such as the secondary topsheets described herein that serve a wicking or storage function. The term absorbent component, however, excludes components that are generally only used as the topsheet or backsheet of the absorbent article.

The measurement of the length of the longest absorbent component taken above should not include any portions of the absorbent component that may be located outboard of, or within any end seal on the sample because these portions of the absorbent component typically serve no absorptive function.

STEP 4

Clamp each end of the sample in the tensile testing apparatus using 3 inch (7.6 cm.) wide clamps. The clamps of the tensile tester are set so that they will be pulled away from each other in opposite directions (that is, they will pull at an angle of 180 degrees). The sample should be centered in the clamps and the clamping pressure should be sufficient to prevent any slippage of the sample in the clamps (this applies to all of the test methods).

The sample should be clamped so that the outermost edge (i.e., the free end) of the clamps are approximately 0.5 inches (about 1.3 cm.) inward from the end edges of the longest absorbent component. The portions of the sample that may be located within or outboard of an end seal on the sample are excluded when determining the location of the end edges of the longest absorbent component for placing the clamps of the testing apparatus on the sample.

STEP 5

Set the gauge length of the tensile tester to the length of the absorbent component (as measured above) less the amount of absorbent component material clamped into each of the clamps (typically 1 inch). Initiate the elongation with a cross head speed of 0.367 inches per second (0.93 cm. per second).

When the sample reaches the gauge length, tare the load cell of the testing apparatus to zero. Set the trigger point to begin collecting data at 20 grams force. (The application of this initial 20 gram force typically pulls out at least some of any slack that may exist in the sample.)

The force and extensibility measurements are taken at the desired times, and the test is completed. The initial length of the sample is the measured length of the longest absorbent component. The force, for the purpose of the appended claims, is the actual force reading on the testing apparatus when the above procedure is followed.

The cutting of the 1.0 inch strips is intended to minimize the effect of any elastic strands in the longitudinal side margins of the absorbent article on the results of the test. (The absorbent articles of the present invention are preferably free of such elastic strands. Optional elastic strands can, however, be added.)

When measured according to this test, 1.0 inch strip of the absorbent article is preferably capable of extension in the longitudinal direction of greater than or equal to about 105%, 110%, 115%, 120%, 125%, or more, of its initial length when subjected to a force of less than or equal to about 20, 50, 100, 150, 200, 300, 400, or 500 grams. The 1.0 inch strip of the absorbent article is preferably capable of extension in the transverse direction when subjected to forces of the same amounts. The strip can have a maximum extension under these forces of up to 110, 120%, 130% 140%, 150%, 160%, 170%, 180%, 190%, 200%, or more. The limits specified in this specification can be combined in any manner in the appended claims.

The absorbent article may be capable of such extension as measured by a 1.0 inch strip in both the longitudinal and transverse directions. In such a case, the absorbent article is preferably extensible in the amounts specified in the foregoing paragraph.

Although the absorbent article can be of any length, preferably, the absorbent article is worn in an undergarment and has a longest absorbent component, such as an absorbent core, with an initial length of less than or equal to about 12.0 inches. The width of the absorbent component of the absorbent article is preferably less than or equal to about 3.0 inches, and is more preferably less than or equal to about 2.5 inches. (Diapers, on the other hand, typically have absorbent cores greater than about 12.0 inches in length and 3.0 inches in width.) In addition, in some embodiments, the absorbent article may have a caliper of less than or equal to about 5 mm.

The absorbent article preferably has a force wall such that the strip requires a force greater than or equal to 1,000 grams to extend beyond 160%, 150%, 140%, 130% of its initial length, or one of the other lengths specified above.

The absorbent article is preferably also elastically extensible or permanently deformable such that when the strip is extended to one of the above lengths, it is capable of recovering to a recovered dimension that is less than or equal its extended length when the extending forces are removed.

B. Method to Measure Extensibility of Absorbent Article.

The sample used for this test is the entire absorbent article. This test is used only to measure the longitudinal extensibility of the absorbent article. The transverse extensibility is measured according to the preceding test method.

The entire absorbent article used as the sample in this test should be tested following steps (2)–(5) above, with the following additional instruction when carrying out step (3).

If the sample cannot be conveniently flattened (such as due to the presence of contracted elastics), the length of the longest absorbent component should be measured by allowing the sample to unfold (if it is folded) and holding the sample in the curved configuration that the sample is in when it is taken out of the box, and measuring the length of the longest absorbent component with a tailor's cloth tape measure along the arc formed by the garment surface of the absorbent article.

The absorbent article is preferably capable of extension in the longitudinal direction (i.e., along the longitudinal centerline) of greater than or equal to about 105%, 110%, 115%, 120%, 125%, 130%, 140%, 150%, 160%, 170%, 180%, 190%, 200%, or more, of its initial length when subjected to a force of less than or equal to about 20, 50, 100, 150, 200, 300, 400, 500, 600, 700, 800, 900, 1,000, or more grams. (The forces for longitudinal extensibility may be higher than those measured on the 1.0 inch strip by the previous test since the entire absorbent article is used in this second test.)

The absorbent article preferably has a force wall such that the strip requires a force greater than or equal to 1,200, 1,500 or 2,000 grams to extend beyond 160%, 150%, 140%, 130% of its initial length, or one of the other lengths specified above.

C. Method to Measure Stretch Relative to Product Shear from an Undergarment.

1. The sample Method—20 Gram Trigger.

The sample used for this test is the entire absorbent article.

Lay the sample unrestrained on a table with the body surface facing upward. Measure the length of the longest absorbent component of the sample to the nearest 0.1 inch (0.25 cm.). Follow the same instructions for measuring the absorbent component in step (3) of Test Methods A and B above. This test, however, is only concerned with the measurement of properties of the sample in the longitudinal direction (i.e., parallel to the longitudinal centerline).

If the sample has an adhesive fastener, remove any adhesive cover strip from the sample. Take a strip of cotton fabric #429W (standard 3 inch width) manufactured by Test Fabrics, Inc. of Middlesex, N.J., and cover 1.0 inch (2.54 cm.) of the fastener at one end of the fastener.

The sample can be placed under an ultraviolet lamp to aid in determining the end of most adhesive fasteners. Eliminate any adhesive tack on the remainder of adhesive fastener by dusting the uncovered portion of the adhesive fastener with talc or corn starch.

The strip of cotton fabric should be long enough so that its free end (unattached end) extends at least 0.5 inch (1.3 cm.) beyond the end edge of the sample (i.e., the actual end edge of the product including absorbent and nonabsorbent components) adjacent to the 1 inch portion of the fastener that the cotton strip covers.

Apply 0.25 psi. of pressure for a period of 30 seconds uniformly (with a weight) to the cotton surface to attach the cotton fabric to the fastener. If the panty fastener is not adhesive, attach the sample to the cotton fabric in the manner the fastener would ordinarily be placed in the wearer's undergarment.

Clamp the end of the sample that is not attached to the cotton strip in the tensile testing apparatus using a 3 inch (7.6 cm.) clamp. The sample should be clamped so that the outermost edge (i.e., the free end) of the clamp is approximately 0.5 inches (about 1.3 cm.) inward from the end edge of the absorbent component. If there is more than one absorbent component, the sample should be clamped so that all of the absorbent components are grabbed by the clamp. In other words, the sample is clamped about 0.5 inches from the end of the absorbent component(s).

Place the free end of the cotton strip into the other 3 inch clamp. The free end of the cotton strip is placed in this clamp so that the free end of the clamp just comes into contact with the nearest end edge of the sample. The clamps of the tensile tester are set so they will pull at 180 degrees (as in the preceding tests). This will impart shearing forces which tend to separate the fastener and the cotton strip from each other.

Set the gauge length of the tensile tester to the length of the absorbent component (measured above) less the amount of absorbent component material clamped into each of the clamps (typically about 0.5 inch). Initiate the elongation with a cross head speed of 0.367 inches per second (0.93 cm. per second). When the sample reaches the gauge length, tare the load cell of the testing apparatus to zero. Set the trigger point to begin collecting data at 20 grams force.

The force and extensibility measurements are taken at the desired times, and the test is completed.

The absorbent article is preferably capable of extending at least about 110%, 115%, 120%, 125%, 130%, 140%, etc. of its initial length before it is subjected to a force of an additional 1,000 grams, or before the forces exerted on the sample cause the fastener to separate from the cotton fabric when tested under the above test (Test Method (C)(1)).

2. Second Method—50 Gram Trigger.

The sample used for this test is the entire absorbent article. This test is only concerned with the measurement of properties of the sample in the longitudinal direction (i.e., parallel to the longitudinal centerline).

Lay the sample unrestrained on a table with the body surface facing downward. If the sample has an adhesive fastener, peel back enough of any adhesive cover strip to expose about 2 inches (about 5 cm.) of adhesive on one end of the sample.

Take a strip of cotton fabric #429W (standard 3 inch width) manufactured by Test Fabrics, Inc. of Middlesex, N.J., and cover 1.0 inch (2.54 cm.) of the (exposed) fastener material at the end of the fastener. The sample can be placed under an ultraviolet lamp to aid in determining the end of most adhesive fasteners. The portion of the fastener covered by the cotton should be representative of the fastening surface. Just place the cotton strip on the fastener. Do not apply pressure at this point.

The strip of cotton fabric should be long enough so that its free end (unattached end) extends at least 0.5 inch (1.3 cm.) beyond the end edge of the sample (i.e., the actual end edge of the product including absorbent and nonabsorbent components) adjacent to the 1.0 inch portion of the fastener that the cotton strip covers. A strip of cotton which extends about 3 inches (about 7.6 cm.) beyond the end edge of the sample is sufficient for many samples.

Measure and mark a transverse line 0.5 inch (1.3 cm.) from the edge of the longest absorbent component at the opposite end of the sample (the end that will be the attached end of the sample). This mark serves as a guide for the location of the clamp of the tensile tester at this end of the sample.

Apply 0.25 psi. of pressure for a period of 30 seconds uniformly {with a foam-covered weight) to the cotton surface to attach the cotton fabric to the fastener. If the panty fastener is not adhesive, attach the sample to the cotton fabric in the manner the fastener would ordinarily be placed in the wearer's undergarment. Remove the weight. Remove any remaining release paper. Eliminate any adhesive tack on the remainder of any adhesive fastener. This may be done by dusting the uncovered portion of the adhesive fastener with talc or corn starch.

Clamp the end of the sample that is not attached to the cotton strip in the tensile testing apparatus using a 3 inch (7.6 cm.) clamp. The sample should be clamped so that the outermost edge (i.e., the free end) of the clamp is 0.5 inches (1.3 cm.) inward from the end edge of the absorbent component. If there is more than one absorbent component in the ½ inch region, the sample should be clamped so that all of the absorbent components are grabbed by the clamp. In other words, the sample is clamped 0.5 inches from the end of the absorbent component(s).

Place the free end of the cotton strip into the other 3 inch clamp. The free end of the cotton strip is placed in this clamp so that the free end of the clamp just comes into contact with the nearest end edge of the sample. Care should be taken not to clamp any portion of this end of the sample. The clamps of the tensile tester are set so they will pull at 180 degrees (as in the preceding tests). This will impart shearing forces which tend to separate the fastener and the cotton strip from each other.

Set the distance between the clamps of the tensile tester so there is excess material (or slack) in the sample. Thus, the sample should not be under tension at this point.

Initiate the elongation a cross head speed of 0.367 inches per second (0.93 cm. per second). If the sample has an adhesive fastener, the elongation should be initiated within 30 seconds after the removal of the 0.25 psi. foam covered weight used to fasten the sample to the cotton strip. Set the trigger point to begin collecting force and elongation data at 50 grams force. The cross head should travel until the cotton separates (i.e., shears) from the 1.0 inch section of the sample's fastener.

The force and extensibility measurements are taken at the desired times, and the test is completed. The gauge length used to calculate % elongation is the linear distance from the free end of the stationary jaw (the jaw that clamps 0.5 inches inward from the end of the absorbent component at the end of the sample opposite the end of the sample adhered to the cotton strip) to the nearest end edge of the cotton fabric when the sample is subjected to 50 grams of tensile force.

The absorbent article is preferably capable of extending at least about 110%, 115%, 120%, 125%, 130%, 140%, etc. of its initial length before it is subjected to a force of an additional 800 or 1,000 grams, or before the forces exerted on the sample cause the fastener to separate from the cotton fabric when tested under the above test (Test Method (C) (2)).

The tests in Test Method C are intended to simulate the conditions under which an absorbent article will stretch when attached to an undergarment.

D. Method to Measure Rate of Return of Absorbent Article Having Elasticity.

The sample used for this test is the entire absorbent article. This test is also only concerned with the measurement of properties of the sample in the longitudinal direction (i.e., parallel to the longitudinal centerline).

Measure the maximum longitudinal extension of the sample at 1,000 grams force using Test Method B above.

The following test is conducted by hand. Remove any adhesive cover strip from the sample. If the sample has an adhesive fastener, eliminate any adhesive tack by dusting the adhesive fastener with talc or corn starch.

Place a ruler with a scale in either 0.1 inch increments or 1 mm. increments on a table.

Grasp one end of the sample with one hand. The end of the sample should be grasped approximately 1 ½ inches (about 3.8 cm.) from the transverse end edge of the product. The sample should be held so that it is as flat and horizontal across its width as possible.

Hold the sample either over the ruler or next to the ruler with the body surface of the sample facing upward so that the scale on the ruler can be observed throughout the test. The sample should be held so that the portions of the sample approximately 0.5 inches (1.3 cm.) inward from this fixed end of the sample are firmly held even with the beginning of the scale on the ruler throughout the test.

Place a digital stop watch which can record time to the nearest 0.01 second next to the ruler and the sample. Position a video camera over the articles on the table so that the sample can be observed and the elapsed time on the stop watch can be simultaneously observed and recorded to the nearest 0.1 second.

Grasp the other transverse end edge (i.e., the free end) of the sample. The sample should be grasped at an area approximately two inches (about 5 cm.) wide centered about the longitudinal centerline. The sample should be grasped in this area about 0.5 inch (about 1.3 cm.) inward from the end edge of longest absorbent component. (The 0.5 inch distance should not include any portion of the absorbent component in or outboard of a product end seal as described above.)

Turn on the video recorder and the stop watch. Gradually extend the free end of the sample so that the sample extends to its maximum extension at 1,000 grams (measured earlier) or to 120% of its original length, whichever is greater. The extension process should be completed in less than or equal to 30 seconds.

Release the free end of the sample. The timing on the stop watch starts when the free end is released.

Determine the distance the sample recovers toward its original length and the time it takes to recover toward its original length at the desired points by playing back the video tape on a video cassette recorder frame by frame and observing any contraction of the sample.

Calculate the rate of recovery by dividing the distance the sample retracts (converted to centimeters) by the time required to travel the corresponding distance. This completes the test.

The sample in Test Method D can also be clamped into the clamps of a tensile testing machine, and the test performed in a similar manner with one end of the sample being placed in a stationary clamp, and the other in a clamp that is capable of instantaneously releasing that end of the sample at the desired time.

When the absorbent article is subjected to tensile forces to extend said absorbent article along its longitudinal centerline to: (a) its maximum extended length at 1,000 grams, or (b) 120% of its original length, whichever is greater, and said tensile forces are removed, said absorbent article, if extended to its maximum extended length, recovers from (a)(i) its maximum extended length toward its recovered length (a) (ii) a distance of its maximum extended length less 10% its original length, or if extended to 120% of its original length, recovers to 110% of its original length at a rate of recovery of less than or equal to about 20, 30, or 40 cm./second.

While particular embodiments of the present invention have been illustrated and described, it would be obvious to those skilled in the art that various other changes and modifications can be made without departing from the spirit and scope of the invention.

What is claimed is:

1. An extensible absorbent article for wearing in the crotch region of an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length cut from said absorbent article along a longitudinal section of said absorbent article that is centered about said longitudinal centerline contains a strip of said absorbent component which has a pair of end edges, and when said 1.0 inch wide strip is clamped 0.5 inches inward from the end edges of said absorbent component, said strip is capable of extension of greater than or equal to about 110% of its initial length when subjected to a force of less than or equal to about 500 grams.

2. An extensible absorbent article for wearing in the crotch region of an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length cut from said absorbent article parallel to said transverse centerline contains a strip of said absorbent component which has a pair of end edges, and when said 1.0 inch wide strip is clamped 0.5 inches inward from the end edges of said absorbent component, said strip is capable of extension of greater than or equal to about 110% of its initial length when subjected to a force of less than or equal to about 500 grams.

3. An extensible absorbent article for attaching to and wearing in an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length cut from said absorbent article along a longitudinal section of said absorbent article that is centered about said longitudinal centerline contains a strip of said absorbent component which has a pair of end edges, and when said 1.0 inch wide strip is clamped 0.5 inches inward from the end edges of said absorbent component, said strip is capable of extension of greater than or equal to about 110% of its initial length when subjected to a force of less than or equal to about 500 grams.

4. The absorbent article of claim 3 wherein said 1.0 inch wide strip is capable of extension to an extended length of between about 110% and 150% of its initial length when subjected to a force of less than or equal to about 400 grams.

5. The absorbent article of claim 4 wherein said 1.0 inch wide strip is capable of extension to an extended length of between about 110% and 140% of its initial length when subjected to a force of less than or equal to about 400 grams.

6. The absorbent article of claim 4 wherein said 1.0 wide strip is capable of extension to an extended length of between about 110% and 150% of its initial length when subjected to a force of less than or equal to about 400 grams.

7. The absorbent article of claim 4 wherein said 1.0 inch wide strip is capable of extension to an extended length of between about 110% and 130% of its initial length when subjected to a force of less than or equal to about 400 grams.

8. The absorbent article of claim 4 wherein said 1.0 inch wide strip is capable of extension to an extended length of between about 110% and 120% of its initial length when subjected to a force of less than or equal to about 400 grams.

9. The absorbent article of claim 8 wherein said 1.0 inch wide strip requires a force of greater than or equal to 1,000 grams to extend beyond 160% of its initial length.

10. The absorbent article of claim 9 wherein said 1.0 inch wide strip requires a force of greater than or equal to 1,000 grams to extend beyond 140% of its initial length.

11. The absorbent article of claim 10 wherein said 1.0 inch wide strip requires a force of greater than or equal to 1,000 grams to extend beyond 130% of its initial length.

12. The absorbent article of claim 3 wherein said 1.0 inch wide strip requires a force of greater than or equal to 1,000 grams to extend beyond 160% of its initial length.

13. The absorbent article of claim 3 wherein a 1.0 inch wide strip having an initial length is cut from a transverse section that runs parallel to the transverse centerline of a second absorbent article of the same type is capable of extension of greater than or equal to about 110% and less than or equal to about 170% of its initial length when subjected to a force of less than or equal to about 400 grams.

14. An extensible absorbent article for attaching to and wearing in an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length cut from said absorbent article along a longitudinal section of said absorbent article that is centered about said longitudinal centerline contains a strip of said absorbent component which has a pair of end edges, and when said 1.0 inch wide strip is clamped 0.5 inches inward from the end edges of said absorbent component, said strip is capable of extension of greater than or equal to about 110% of its initial length when subjected to a force of less than or equal to about 300 grams.

15. The absorbent article of claim 14 capable of extension greater than about 110% of its initial length when subjected to a force of less than or equal to about 200 grams.

16. The absorbent article of claims 14 or 15 wherein said absorbent component has an initial length of less than or equal to about 12.0 inches.

17. The absorbent article of claim 14 wherein when said 1.0 inch wide strip is extended to an extended length that is greater than or equal to 150% of its initial length, said strip will recover to a dimension that is less than or equal to 150% of its initial length when extending forces are removed.

18. The absorbent article of claim 14 wherein when said 1.0 inch wide strip is extended to an extended length that is greater than or equal to 120% of its initial length, said strip will recover to a dimension that is less than or equal to 120% of its initial length when extending forces are removed.

19. An extensible absorbent article for wearing in the crotch region of an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length is cut from a longitudinal section of said absorbent article that is centered about said longitudinal centerline contains a strip of said absorbent component which has a pair of end edges, and when said 1.0 inch wide strip is clamped 0.5 inches inward from the end edges of said absorbent component, said strip is capable of extension that is:
  (i) greater than or equal to about 105% of its initial length when subjected to a force of less than or equal to about 150 grams, and
  (ii) greater than or equal to about 120% of its initial length when subjected to a force less than or equal to about 400 grams.

20. An extensible absorbent article for attaching to and wearing in an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length and an extended length cut from said absorbent article along a transverse section of said absorbent article that runs parallel to the transverse centerline of said absorbent article contains a strip of said absorbent component which has a pair of end edges, and when said 1.0 inch wide strip is clamped 0.5 inches inward from the end edges of said absorbent component, said strip is capable of extension to an extended length of between about 110% to about 170% of its initial length when subjected to a force of less than or equal to about 500 grams.

21. An extensible absorbent article for attaching to and wearing in an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length and an extended length cut from said absorbent article along a transverse section of said absorbent article that runs parallel to the transverse centerline of said absorbent article contains a strip of said absorbent component which has a pair of end edges, and when said 1.0 inch wide strip is clamped 0.5 inches inward from the end edges of said absorbent component, said strip is capable of extension to an extended length of between about 110% to about 140% of its initial length when subjected to a force of less than or equal to about 300 grams.

22. An extensible absorbent article for attaching to and wearing in an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length and an extended length cut from said absorbent article along a transverse section of said absorbent article that runs parallel to the transverse centerline of said absorbent article contains a strip of said absorbent component which has a pair of end edges, and when said 1.0 inch wide strip is clamped 0.5 inches inward from the end edges of said absorbent component, said strip is capable of extension to an extended length of between about 110% to about 150% of its initial length when subjected to a force of less than or equal to about 500 grams.

23. An extensible absorbent article for attaching to and wearing in an undergarment and extending with the crotch region of said undergarment, said absorbent article having a longitudinal centerline, a transverse centerline, a liquid pervious side, a liquid impervious side, and an absorbent component positioned between said liquid pervious side and said liquid impervious side, wherein a 1.0 inch wide strip having an initial length and an extended length cut from said absorbent article along a transverse section of said absorbent article that runs parallel to the transverse centerline of said absorbent article contains a strip of said absorbent component which has a pair of end edges, and when said 1.0 inch wide strip is clamped 0.5 inches inward from the end edges of said absorbent component, said strip is capable of extension to an extended length of between about 110% to about 150% of its initial length when subjected to a force of less than or equal to about 300 grams.

24. An extensible absorbent article for attaching to and wearing in an undergarment and extending with the crotch region of said undergarment, said absorbent article having a longitudinal centerline, two transverse end edges, a liquid pervious side, a liquid impervious side, an absorbent component positioned between said liquid pervious side and said liquid impervious side, said absorbent component having two transverse end edges, one adjacent each transverse end edge of the absorbent article, and a fastener for attaching said absorbent article to an undergarment, said fastener having two transverse ends, wherein when one of said transverse end edges of said absorbent article is clamped with a stationary clamp 0.5 inch inward from the adjacent transverse end edge of said absorbent component, and said fastener has one end adjacent said stationary clamp and one end opposite said stationary clamp, and one end of a strip of cotton fabric is attached to a 1.0 inch section of said fastener at the end of the fastener opposite said stationary clamp, and the other end of the cotton strip is pulled in the direction of the longitudinal centerline of the absorbent article that is 180 degrees opposite the orientation of the end of the absorbent article clamped in the stationary clamp, and said absorbent article has an initial length measured when the absorbent article is subjected to a force of 50 grams, the portion of said absorbent article containing said absorbent component will extend at least about 130% of its initial length before the absorbent article shears from the cotton fabric.

25. An extensible absorbent article for attaching to and wearing in an undergarment and extending with the crotch region of said undergarment, said absorbent article having a longitudinal centerline, two transverse end edges, a liquid pervious side, a liquid impervious side, an absorbent component positioned between said liquid pervious side and said liquid impervious side, said absorbent component having two transverse end edges, one adjacent each transverse end edge of the absorbent article, and a fastener for attaching said absorbent article to an undergarment, said fastener having two transverse ends, wherein when one of said transverse end edges of said absorbent article is clamped with a stationary clamp 0.5 inch inward from the adjacent transverse end edge of said absorbent component, and said fastener has one end adjacent said stationary clamp and one end opposite said stationary clamp, and one end of a strip of cotton fabric is attached to a 1.0 inch section of said fastener at the end of the fastener opposite said stationary clamp, and the other end of the cotton strip is pulled in the direction of the longitudinal centerline of the absorbent article that is 180 degrees opposite the orientation of the end of the absorbent article clamped in the stationary clamp, and said absorbent article has an initial length measured when the absorbent article is subjected to a force of 50 grams, the portion of said absorbent article containing said absorbent component will extend at least about 125% of its initial length upon the application of additional stretching forces before: (a) said absorbent article is subjected to a force of 800 additional grams, or (b) the absorbent article is subjected to a force that causes its fastener to separate from the cotton fabric.

26. An extensible absorbent article for attaching to and wearing in an undergarment and extending with the crotch region of said undergarment, said absorbent article having a longitudinal centerline, two transverse end edges, a liquid pervious side, a liquid impervious side, an absorbent component positioned between said liquid pervious side and said liquid impervious side, said absorbent component having two transverse end edges, one adjacent each transverse end edge of the absorbent article, and a fastener for attaching said absorbent article to an undergarment, said fastener having two transverse ends, wherein when one of said transverse end edges of said absorbent article is clamped with a stationary clamp 0.5 inch inward from the adjacent transverse end edge of said absorbent component, and said fastener has one end adjacent said stationary clamp and one end opposite said stationary clamp, and one end of a strip of cotton fabric is attached to a 1.0 inch section of said fastener at the end of the fastener opposite said stationary clamp, and the other end of the cotton strip is pulled in the direction of the longitudinal centerline of the absorbent article that is 180 degrees opposite the orientation of the end of the absorbent article clamped in the stationary clamp, and said absorbent article has an initial length measured when the absorbent article is subjected to a force of 20 grams, the portion of said absorbent article containing said absorbent component will extend at least about 115% of its initial length upon the application of additional stretching forces before: (a) said absorbent article is subjected to a force of 1,000 additional grams, or (b) the absorbent article is subjected to a force that causes its fastener to separate from the cotton fabric.

27. The absorbent article of claim 26 wherein said absorbent article is capable of extending at least about 120% of its initial length.

* * * * *